(12) United States Patent
Dang et al.

(10) Patent No.: US 8,613,917 B2
(45) Date of Patent: *Dec. 24, 2013

(54) COMBINATION BACTERIOLYTIC THERAPY FOR THE TREATMENT OF TUMORS

(75) Inventors: Long Dang, Baltimore, MD (US); Chetan Bettegowda, Towson, MD (US); Kenneth W. Kinzler, Bel Air, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 83 days.

This patent is subject to a terminal disclaimer.

(21) Appl. No.: 13/198,850

(22) Filed: Aug. 5, 2011

(65) Prior Publication Data

US 2011/0311500 A1 Dec. 22, 2011

Related U.S. Application Data

(63) Continuation of application No. 10/568,765, filed as application No. PCT/US2004/034625 on Oct. 21, 2004, now Pat. No. 8,007,782.

(60) Provisional application No. 60/512,923, filed on Oct. 22, 2003.

(51) Int. Cl.
| | |
|---|---|
| A61K 35/00 | (2006.01) |
| A01N 63/00 | (2006.01) |
| A01N 63/02 | (2006.01) |
| C12N 1/20 | (2006.01) |
| C12N 3/00 | (2006.01) |

(52) U.S. Cl.
USPC ..... 424/93.41; 424/780; 435/242; 435/252.7; 435/842

(58) Field of Classification Search
None
See application file for complete search history.

(56) References Cited

U.S. PATENT DOCUMENTS

| | | | |
|---|---|---|---|
| 5,554,638 | A | 9/1996 | Dewhirst et al. |
| 5,688,517 | A | 11/1997 | Helson et al. |
| 7,344,710 | B2 | 3/2008 | Dang et al. |
| 2003/0103987 | A1 | 6/2003 | Von Eichel-Streiber et al. |

FOREIGN PATENT DOCUMENTS

| | | |
|---|---|---|
| WO | 03/045131 A2 | 6/2003 |
| WO | 2005/039491 A2 | 5/2005 |

OTHER PUBLICATIONS

L. Dang et al., "Combination Bacteriolytic Therapy for the Treatment of Experimental Tumors," Proceedings of the National Academy of Sciences of USA, Dec. 18, 2001; vol. 98, No. 26, pp. 15155-15160.
J. Theys et al., "Improvement of *Clostridium* Tumor Targeting Vectors Evaluated in Rat Rhabdomyosarcomas," FEMS Immunology and Medical Microbiology, Feb. 1, 20001, vol. 30, No. 1, pp. 37-41.
N.P. Minton et al., "Clostridia in Cancer Therapy," Clostridia Biotechnology and Medical Applications, Feb. 15, 2001, pp. 251-270.
T. Fojo et al., "Taxol and Other Microtubule-Interactive Agents," Current Opinion in Oncologic, Endocrine and Metabolic-investigational Drugs, Jan. 1, 2001, vol. 2, No. 3, pp. 293-304.
R. F. Service, "Chemical Synthesis: Tumor-Killer Made: How Does It Work?" Science, Dec. 20, 1996, vol. 274, No. 5295, pp. 2009.
F. Valeriote et al., "Synergistic Interaction of Anticancer Agents: A Cellular Perspective," Cancer Chemotherapy Reports, Sep. 1, 1975, vol. 59, No. 5, pp. 895-900.
L. Dang et al., "Targeting Vascular and Avascular Compartments of Tumors with C, novyi-NT and Anti-Microtubule Agents," Cancer Biology & Therapy, Mar. 2004, vol. 3, No. 3., pp. 326-337.

*Primary Examiner* — Debbie K Ware
(74) *Attorney, Agent, or Firm* — Banner & Witcoff, Ltd

(57) ABSTRACT

Current approaches for treating cancer are limited, in part, by the inability of drugs to affect the poorly vascularized regions of tumors. We have found that spores of anaerobic bacteria in combination with agents which interact with microtubules can cause the destruction of both the vascular and avascular compartments of tumors. Two classes of microtubule inhibitors were found to exert markedly different effects. Some agents that inhibited microtubule synthesis, such as vinorelbine, caused rapid, massive hemorrhagic necrosis when used in combination with spores. In contrast, agents that stabilized microtubules, such as the taxane, docetaxel, resulted in slow tumor regressions that killed most neoplastic cells. Remaining cells in the poorly perfused regions of tumors could be eradicated by sporulated bacteria. Mechanistic studies showed that the microtubule destabilizers, but not the microtubule stabilizers, radically reduced blood flow to tumors, thereby enlarging the hypoxic niche in which spores could germinate. A single intravenous injection of spores plus selected microtubule-interacting agents was able to cause regressions of several tumors in the absence of excessive toxicity.

21 Claims, 16 Drawing Sheets

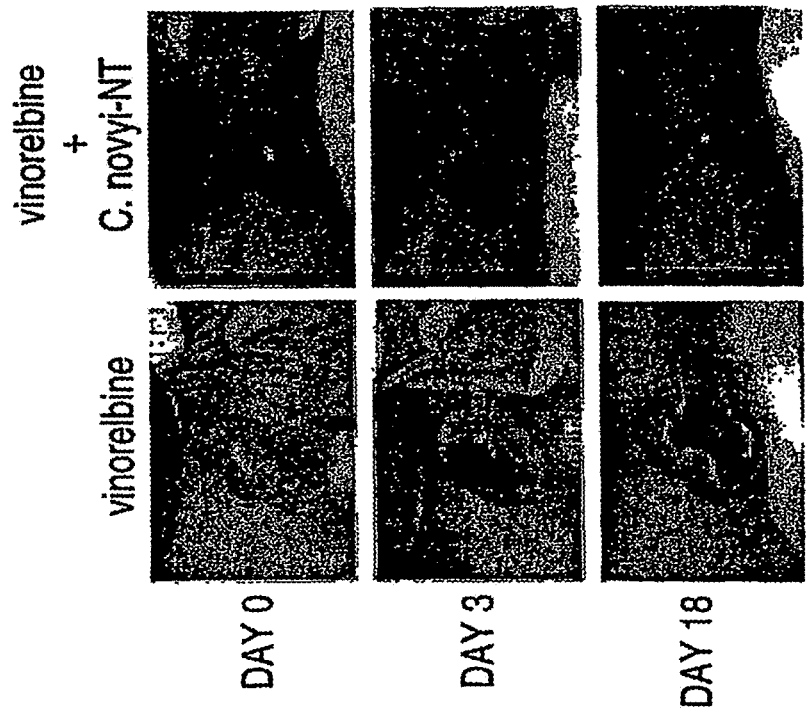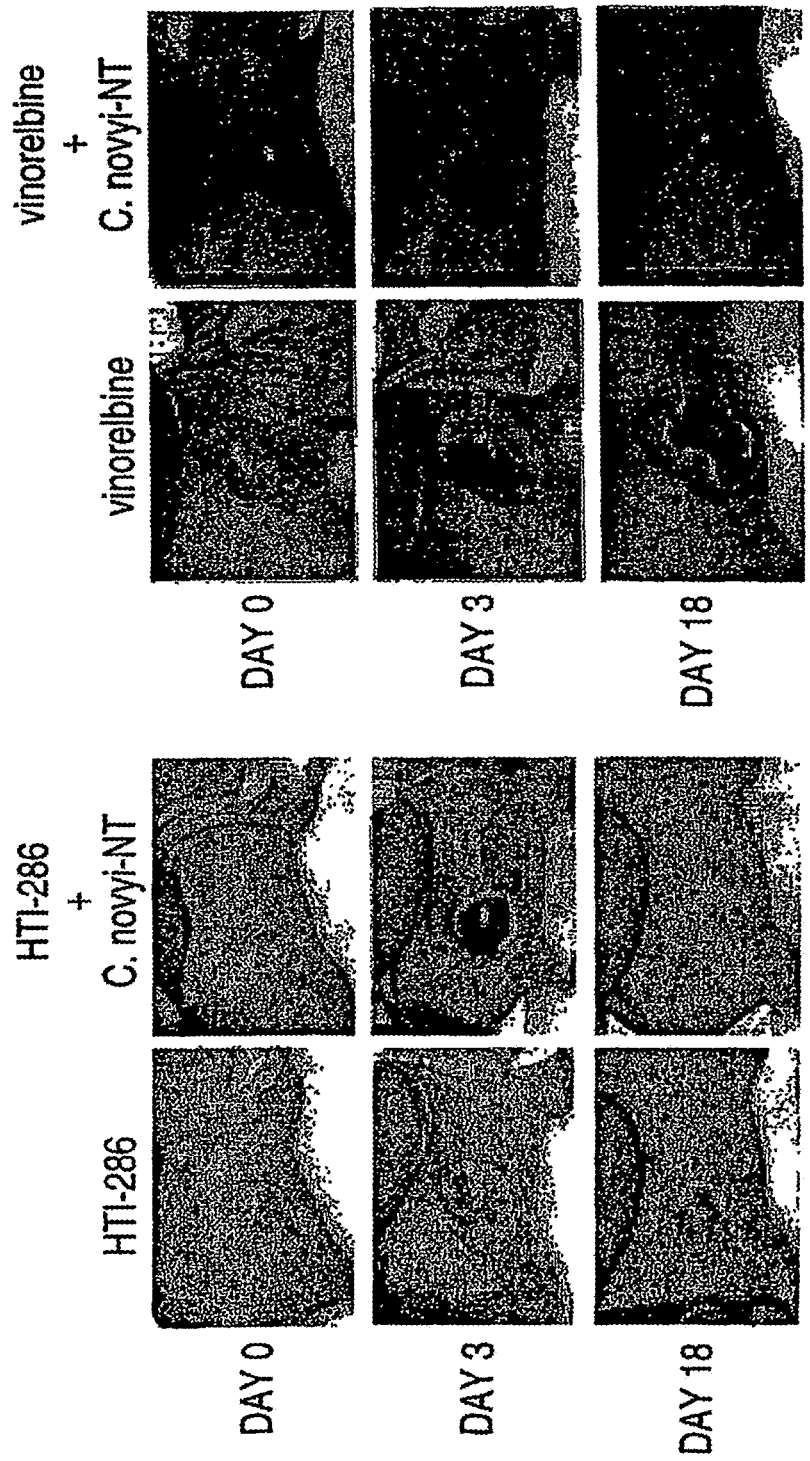

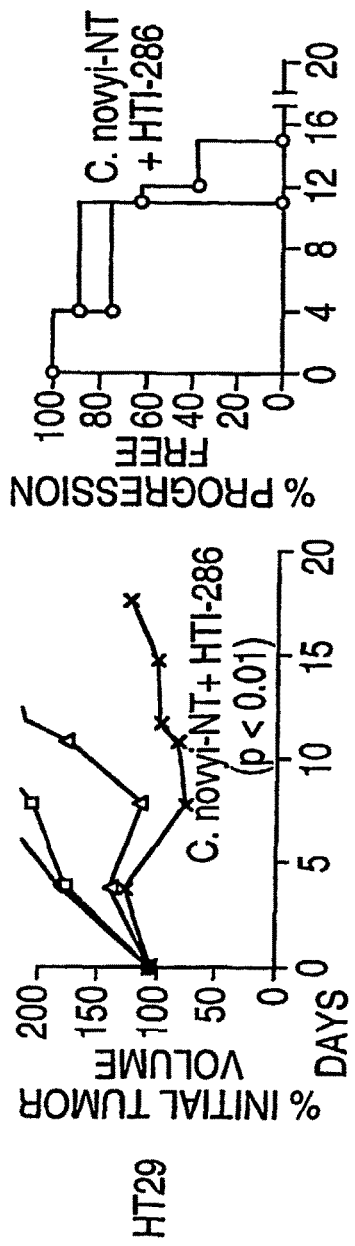
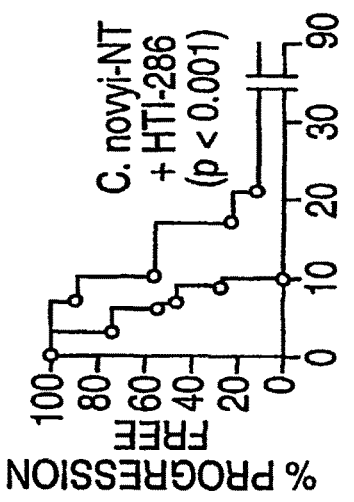
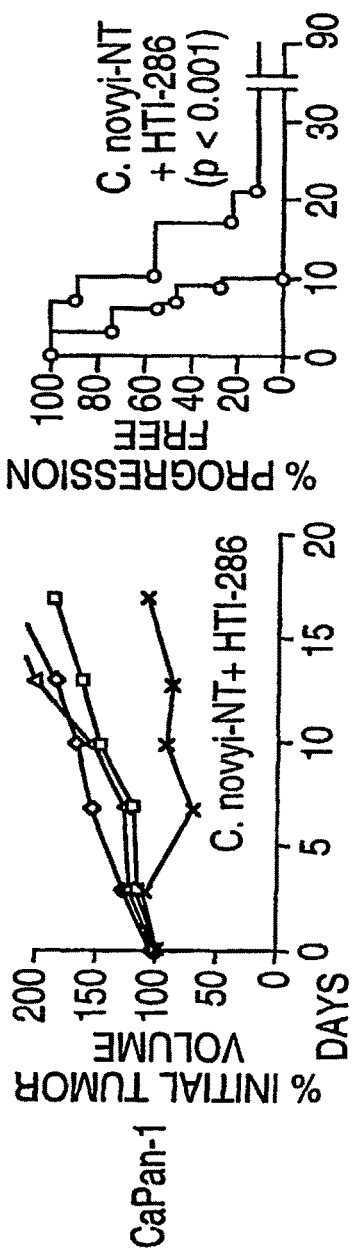

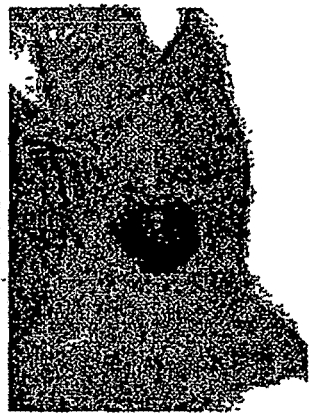
FIG. 4B HuCC-T1
FIG. 4D HT-29
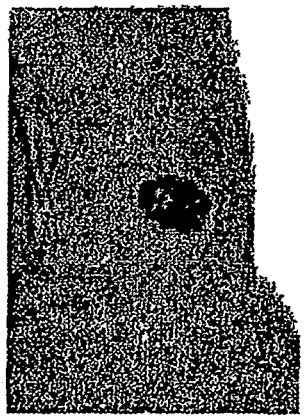
FIG. 4A CaPan-1
FIG. 4C SW480

TUMOR VOLUME

KAPLAN-MEIER

KAPLAN-MEIER

TUMOR VOLUME

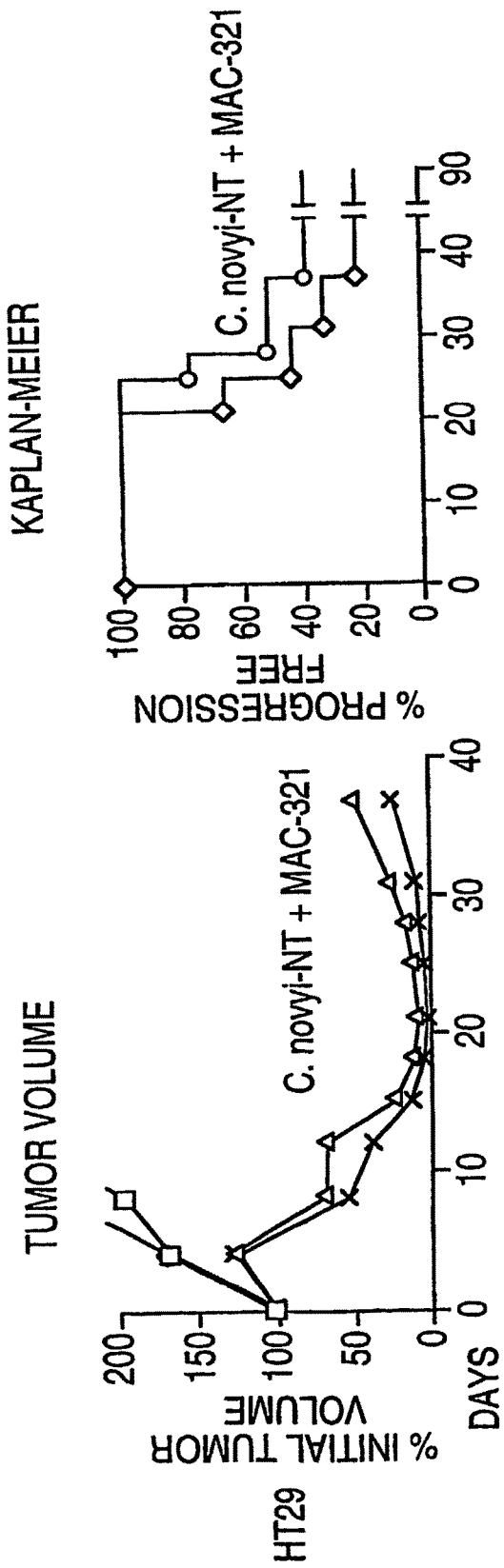

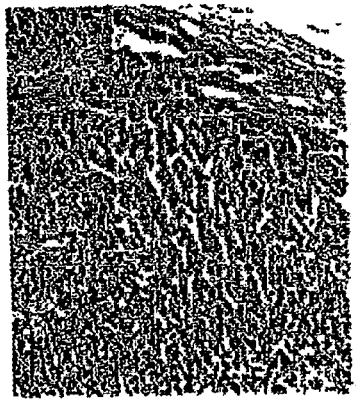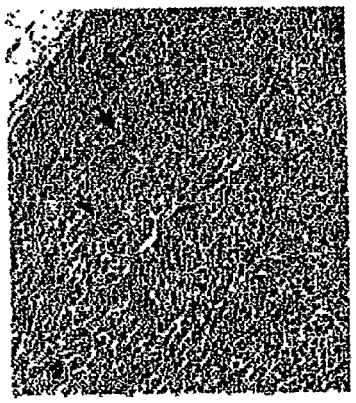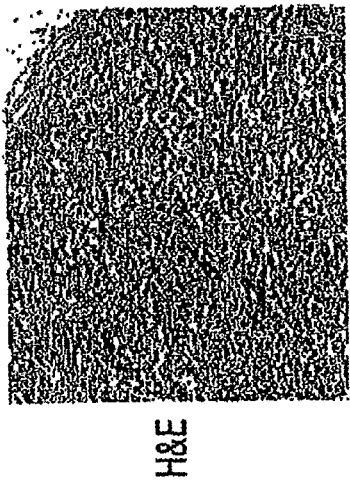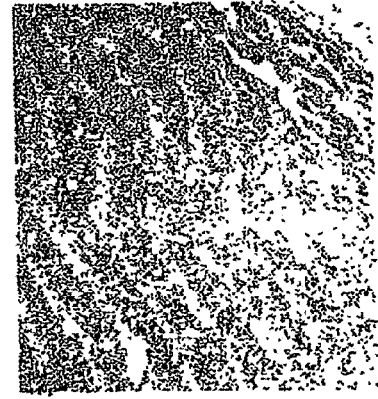

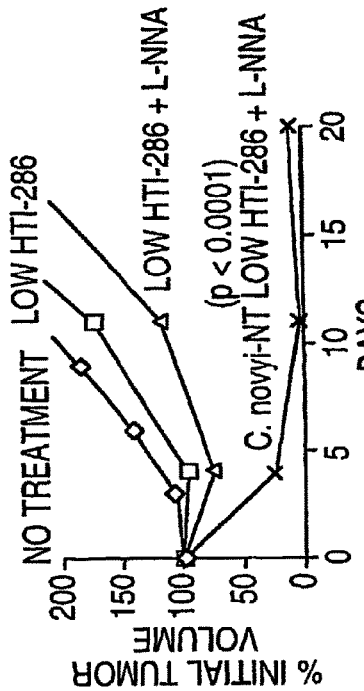
FIG. 10B HuCC-T1
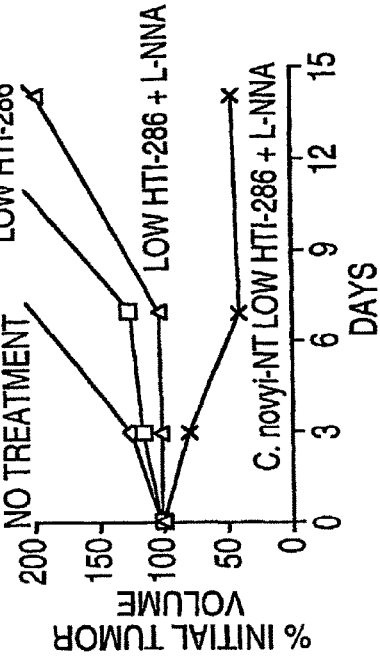
FIG. 10D SW480
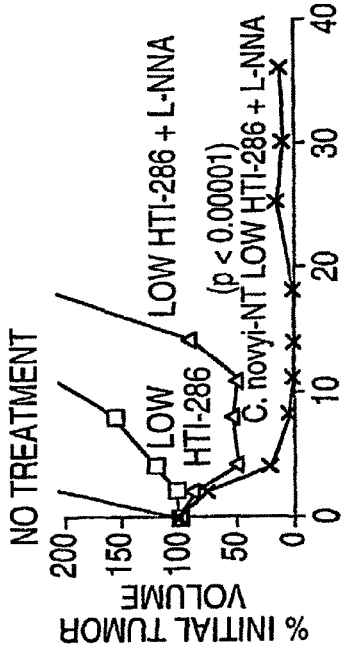
FIG. 10A HCT116
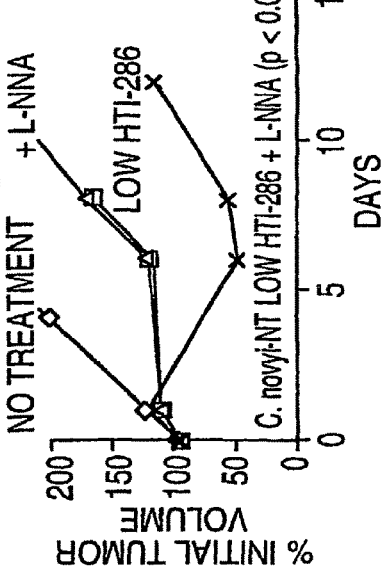
FIG. 10C HT29

| COMPOUND | R₁= | R₂= | R₃= |
|---|---|---|---|
| PACLITAXEL | H | CH₃C(O)- | benzamido phenyl hydroxy group |
| DOCETAXEL | H | H | Boc-amino phenyl hydroxy group |
| MAC-321 | CH₃CH₂C(O)- | H | Boc-amino furyl hydroxy group |

FIG. 12
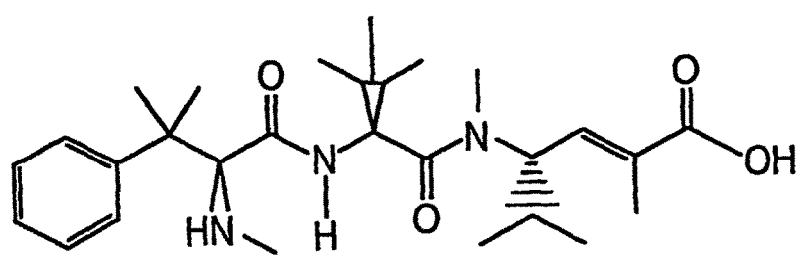
HTI-286
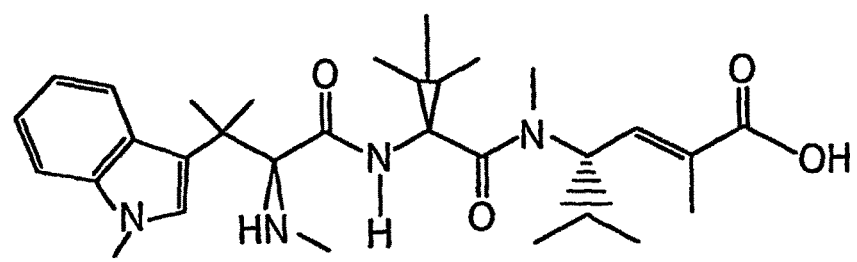
hemiasterlin

COMBINATION BACTERIOLYTIC THERAPY FOR THE TREATMENT OF TUMORS

This invention was made using U.S. government support from NIH grant CA 62924. The U.S. government therefore retains certain rights in the invention.

TECHNICAL FIELD OF THE INVENTION

This invention is related to the field of oncology. In particular it relates to combined biological and chemical treatments of tumors.

BACKGROUND OF THE INVENTION

The prognosis for patients who present with advanced cancers of the pancreas, colon, lung, breast, ovary, brain or prostate is dismal. This tragic situation has stimulated an avalanche of research, resulting in a revolution in understanding cancer pathogenesis, significant gains in the applications of conventional chemotherapeutic agents, and some promising new agents. Unfortunately, this revolution has not yet had a major impact on the treatment of common solid tumors. Many believe that the best hope for future therapeutic gains lies in combining novel approaches with more conventional agents. Our laboratory has been attempting to determine whether spores of C. novyi-NT, a strain of anaerobic bacteria, can be used in such a fashion.

The rationale for using anaerobic bacteria lies in the unique angiogenic state that exists within tumors. It is widely recognized that solid tumors require angiogenesis to grow to a clinically important size (Folkman, 2002; Kerbel, 2000). It is less often appreciated that solid tumors almost always outpace angiogenesis, often resulting in large regions that are poorly vascularized (Brown, 2002). These poorly perfused regions pose major problems for the oncologist. Drug delivery is compromised and drug efficacy suffers not only from the lower drug concentrations reached in avascular areas but also from the fact that many chemotherapeutic agents rely both on oxygen and on actively replicating tumor cells for full potency (Brown and Giaccia, 1998).

The potential of anaerobic bacteria for treating cancer was recognized a half century ago (Jain and Forbes, 2001). Though initial clinical trials of such organisms were discouraging, this approach has more recently been revisited using genetic engineering techniques not available in the past (Heppner and Mose, 1978). For example, a strain of the facultative anaerobe S. typhi was created in which the major endotoxin component was mutated, resulting in a substantial diminution of toxicity (Low et al., 1999). Similarly, a cytosine deaminase gene was introduced into the anaerobe Clostridium sporogenes, endowing these bacteria with potent anti-tumor effects when used in combination with fluorocytosine, a prodrug activated by the introduced gene (Liu et al., 2002). Our group has eliminated the major systemic toxin gene from the strict anaerobe C. novyi, creating a strain called C. novyi-NT that had anti-neoplastic activities when combined with selected chemotherapeutic agents (COBALT, for combination bacteriolytic therapy (Dang et al., 2001).

In a previous study of various chemotherapeutic agents the anti-microtubule agent dolastatin-10, was found to be particularly effective when used in combination with C. novyi-NT spores, though toxicity was problematic (Dang et al., 2001). The mechanistic basis for this efficacy was not known. There is a need in the art for a systematic exploration of the relationship between various anti-microtubule agents and bacteriolytic therapy.

SUMMARY OF THE INVENTION

According to a first embodiment a method is provided for treating tumors in a mammal. Spores of a toxin-defective anaerobic bacterium are adminstered to the mammal. A microtubule stabilizing anti-tumor agent is also administered to the mammal. As a result of the treatment, the tumor regresses or its growth is slowed or arrested.

According to a second embodiment a kit for treating tumors is provided. The components of the kit are in a divided or undivided container. The components comprise spores of an anaerobic bacterium which is toxin-defective and an agent which stabilizes microtubules.

These and other embodiments of the invention which will be apparent to those of skill in the art upon reading the specification provide the art with an exciting modality for treating mammals including patients with tumors. These modalities cause striking tumor regressions without excessive toxicity.

BRIEF DESCRIPTION OF THE DRAWINGS

FIGS. 1A and 1B Anatomic effects of drugs that destabilize microtubules on HCT116 tumors
Photographs of mice bearing HCT116 xenografts after treatment on day 0 with the microtubule destabilizers HTI-286 at 1.7 mg/kg (FIG. 1A) or vinorelbine at 20 mg/kg (FIG. 1B) with or without C. novyi-NT.

FIGS. 3A through 3H Quantification of the effects of C. novyi-NT and HTI-286 in mice bearing various xenografts
Animals (n>6 for each arm) were treated with HTI-286+/−C. novyi-NT spores. The dose of HTI-286 (1.7 to 2 mg/kg) used to treat each xenograft type was the smallest dose required to see significant effects when administered alone. Tumor growth curves (FIGS. 3A, 3C, 3E, and 3G) and progression free survival (Kaplan-Meier plots, FIGS. 3B, 3D, 3F, and 3H) are shown. Light blue: untreated control; Purple: C. novyi-NT spores alone; Green: drug alone: Red: drug plus C. novyi-NT spores. The p-values are based on comparisons between drug alone and drug+C. novyi-NT spores. The p-value is indicated only when the result was statistically significant.

FIG. 4A-4D Anatomic effects of drugs that destabilize microtubules on various xenografts (CaPan-1, HuCC-T1, SW480, and HT-29, respectively)
Photographs of mice bearing the indicated xenografts were treated with C. novyi-NT with HTI-286 and photographed 3 days later.

FIGS. 7A through 7F Quantification of the effects of *C. novyi*-NT and MAC-321 in mice bearing various xenografts. Animals (n>6 for each arm) were treated with MAC-321+/− *C. novyi*-NT. The dose of MAC-321 (45 to 70 mg/kg) was optimized for each xenograft type; for example, HuCC-T1 was more sensitive to MAC-321 than were the other tumor types. Tumor growth curves (FIGS. 7A, 7C and 7E) and progression free survival (Kaplan-Meier plots, FIGS. 7B, 7D and 7F) are shown. Color code same as in FIGS. 3A through 3H. The p-values are based on comparisons between drug alone and drug+*C. novyi*-NT spores. The p-value is indicated only when the result was statistically significant.

FIGS. 9A through 9F Effect of docetaxel and HTI-286 on Glut-1 expression.
Mice bearing subcutaneous xenografts of HCT116 cells, 400-500 mm3 in size, were intravenously injected with HTI-286 (1.7 mg/kg; FIGS. 9B, 9E) or docetaxel (50 mg/kg; FIGS. 9C, 9F). Mice were euthanized six hours after treatment. Tumors were sectioned and H & E stained. Adjacent sections were stained for Glut-1 expression, a marker for hypoxia. Cells positive for Glut-1 appear brown. Arrows indicate examples of hemorrhage.

FIG. 10A-10F Quantification of the effects of *C. novyi*-NT plus low doses of HTI-286 and L-NNA on various xenografts (HCT116, HuCC-T1, HT-29, SW480, B16, and DLD-1, respectively).
Animals (n>6 for each arm) were treated with HTI-286 (1 mg/kg)+L-NNA (10 mg/kg)+/−*C. novyi*-NT. HTI-286 at this dose had no significant effects on tumor growth when administered without L-NNA, and vice versa. The p-values are based on comparisons between L-NNA+HTI-286 and L-NNA+HTI-286+*C. novyi*-NT spores. The p-value is indicated only when the result was statistically significant.

FIG. 12 Chemical structures of HTI-286 and hemiasterlin.

DETAILED DESCRIPTION

Figure 2A:
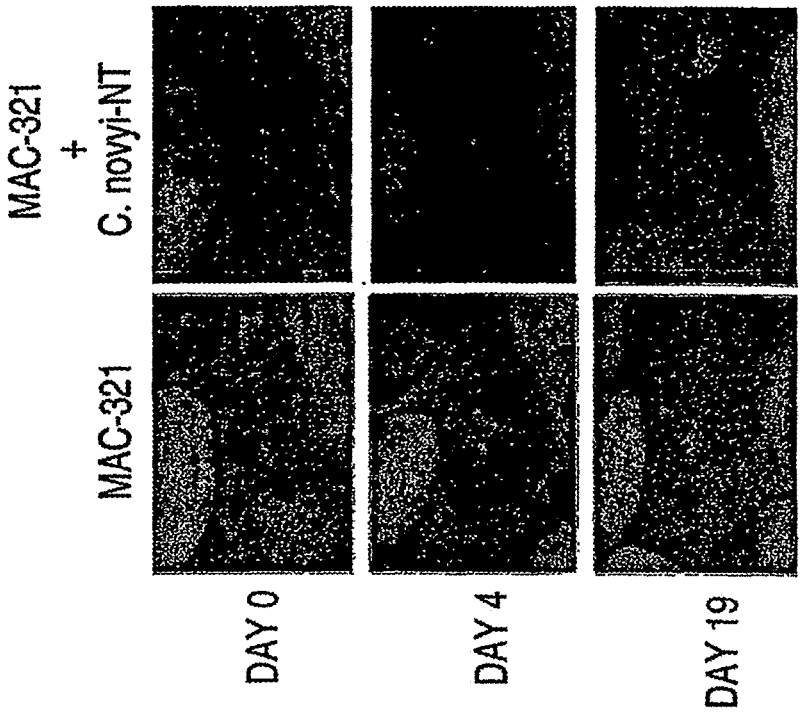
FIGS. 2A and 2B Anatomic effects of drugs that stabilize microtubules on HCT 116 tumors
Photographs of mice bearing HCT116 xenografts after treatment on day 0 with the microtubule stabilizing agents docetaxel at 50 mg/kg (FIG. 2A) or MAC-321 (FIG. 2B) at 60 mg/kg with or without C. novyi-NT.

The tumor microenvironment is heterogeneous. Oxygen concentrations within single tumors vary widely and can dramatically alter the responses to therapies. We have targeted the poorly vascular regions of tumors with an anerobic bacterium and the vascular regions of tumors with either microtubule stabilizing or destabilizing agents. We found that we could achieve major regressions and cures when these drugs were combined with spores of anaerobic bacteria, but that the mechanisms underlying the efficacy varied with the class of drug used. Specific agents that target different tumor microenvironments can be combined to produce enhanced therapeutic results.

The bacteria useful in the practice of the present invention are anaerobic spore-formers. Suitable genera include but are not limited to Bifidobacteria, Lactobacilli, and Clostridia. A number of species of these bacteria have been tested for their ability to grow in tumors in a robust and dispersed manner. *Clostridium novyi* and *Clostridium sordelii* were found to be the best of the strains we tested for these properties. Other strains and species having suitable characteristics can be used as well.

Decreasing the natural production of toxins is desirable in using bacteria therapeutically. While toxin-defective strains need not be totally non-toxigenic, it is desirable that at least one of the toxin genes by mutated, deleted, or otherwise inactivated to render the bacteria less harmful to the host. Preferably the toxicity is reduced by a factor of at least 2, 5, 10, 50, 100, or 1000. If a toxin gene is episomal or on a phage, then curing of the episome or phage can be used to delete the toxin gene. Techniques are well known in the art for mutagenesis, curing, and screening of mutants.

Isolated and bacteriologically pure vegetative bacteria or spores, according to the invention are those which are not contaminated with other bacteria or spores. Microbiological techniques for obtaining such pure cultures are will known in the art. Typically single colonies are picked and spread upon an agar nutrient medium, separating colonies so that new colonies arise that are the progeny of single cells. This process is typically repeated to ensure pure cultures. Alternatively, liquid cultures can be serially diluted and plated for single colony formation. Serial repetition is desirable to ensure colony formation from single cells. See, e.g., J. H. Miller, Experiments in Molecular Genetics, Cold Spring Harbor Laboratory, NY, 1972.

Spores can be administered to a tumor-bearing mammal by any means which will afford access to the tumor. Spores can be injected intravenously, intradermally, subcutaneously, intramuscularly, intraperitoneally, intratumorally, intrathecally, surgically, etc. Preferred techniques are intravenous and intratumoral injections. Tumor bearing mammals can be humans, pets, such as dogs and cats, agricultural animals such as cows, sheep, horses, goats and pigs, and laboratory animals, such as rats, hamsters, monkeys, mice, and rabbits. The tumors to be treated are preferably large enough to have outgrown their blood supply and contain necrotic regions. This factor should not be limiting for most human tumor situations, as the great majority of clinically apparent human tumors have large necrotic regions within them.

Combination treatment involves administering anaerobic spores as well as a second anti-tumor agent. Together these agents produce a greater or more long-lasting decrease in the growth of the tumor. Second anti-tumor agents which can be used include any which are known in the art. Such anti-tumor agents include but are not limited to agents which stabilize microtubules, agents which collapse tumor vasculature, typically by inhibiting synthesis of microtubules, radiation, and anti-tumor antigen antibodies. These anti-tumor agents are administered according to the conventional means used in the art of medical and radiation oncology. The agents can be administered in any order or simultaneously. It may be desirable, however, to administer the spores prior to administering the second anti-tumor agent. If agents are to be administered serially, they are preferably administered within a span of a month, more preferably within a span of a fortnight, and even more preferably within a span of a week. Optimization of the time span is well within the skill of the art. Moreover, multiple anti-tumor agents can be administered in conjunction with the spores. Thus it may be desirable in order to achieve even greater reduction in tumor growth that a plurality of anti-tumor agents be used. Anti-tumor agents from different categories or mechanisms may achieve superior results. Thus a preferred combination includes spores and a microtubule stabilizing agent.

Anti-tumor agents which stabilize microtubules include, but are not limited to the taxanes, such as 10-deacetyltaxol; 7-epi-10-deacetyltaxol; 7-xylosyl-10-deacetyltaxol; 7-epitaxol; cephalomannine; baccatin III; baccatin V; 10-deacetylbaccatin III; 7-epi-10-deacetylbaccatin III; 2-debenzoyl-2-(p-trifluoromethylbenzoyl)taxol; and 20-acetoxy-4-deacetyl-5-epi-20,O-secotaxol. Other microtubule stabilizers which can be used include arsenic trioxide, discodermolide, epothilone B, and (+)-14-normethyldiscodermolide.

Anti-tumor agents which function to collapse tumor vessels include but are not limited to vinblastine, vincristine, colchicine, combrestatin A4P, dolastatin-10, auristatin PE, auristatin PHE, D-24851, HTI-286, noscapine, vinorelbine, and 5,6 dimethylxanthenone-4-acetic acid. Others as are known or discovered with the same function can be used. Such agents are believed to function by inhibiting the synthesis of microtubules.

Nitric oxide synthetase inhibitors, especially inhibitors of the eNOS isoform of the enzyme, can be used to potentiate the effects of the microtubule-interacting drugs. Suitable inhibitors include but are not limited to L-NNA, NG-monomethyl-L-arginine (L-NMMA), and L-NAME.

Kits comprising the useful components for practicing the anti-tumor methods of the present invention can be packaged in a divided or undivided container, such as a carton, bottle, ampule, tube, etc. The spores and anti-tumor agents can be packaged in dried, lyophilized, or liquid form. Additional components provided can include vehicles for reconstitution of dried components. Preferably all such vehicles are sterile and apyrogenic so that they are suitable for injection into a mammal without causing adverse reactions. The anti-tumor agents other than the spores are also preferably sterile. The spores are preferably microbiologically pure, i.e., containing no other bacteria other than the desired spore-forming anaerobe. Instructions for practicing the method of the invention may be included in the kit, in paper or electronic medium. A reference to a website that teaches the method may also be provided.

The above disclosure generally describes the present invention. A more complete understanding can be obtained by reference to the following specific examples which are provided herein for purposes of illustration only, and are not intended to limit the scope of the invention.

EXAMPLE 1

Materials & Methods

Drugs

Dolastatin 10, auristatin 15-PE, auristatin PYE, and pancratistatin 7-O-phosphate were synthesized by Dr. G. R. Pettit (Cancer Research Institute, Arizona State University, AZ) (Pettit, 1997). Discodermolide, (+)-14-normethyldiscodermolide synthesized by Dr. A. Smith (University of Pennsylvania, PA) (Smith et al., 2000). Epothilone B was synthesized by S. Danishevsky, Memorial Sloan-Kettering Cancer Center, New York, N.Y. (Altmann, 2003). HTI-286 [N,β,β-trimethyl-L-phenylalanyl-$N^1$-[(1S,2E)-3-carboxy-1-isopropylbut-2-enyl]-$N^1$, 3-dimethyl-L-valinamide] was synthesized at Wyeth Research, Pearl River, N.Y. (Loganzo et al., 2003). MAC-321 [5β, 20-epoxy-1, 2α-, 4-, 7β-, 10β-, 13α-hexahydroxytax-11-en-9-one 4 acetate 2 benzoate 7 propionate 13-ester with (2R,3S)—N-tertbutoxycarbonyl-3-(2-furyl)isoserine](Sampath et al., 2003) was synthesized by Taxolog, Inc (Fairfield, N.J.). Combretastatin A4P and D-24851 were synthesized by Saeed Khan, Sidney-Kimmel Comprehensive Cancer Center, Baltimore, Md. Synthetic methods are cited in the references listed in Table 1. Vincristine, vinblastine, vinorelbine, paclitaxel, and docetaxel were purchased from the Johns Hopkins Hospital Pharmacy. Colchicine, noscapine, arsenic trioxide, and L-NNA were purchased from Sigma (St. Louis, Mo.).

Cell Lines and Animals

Female athymic nude and C57BL/6 mice 6 to 8 weeks of age were purchased from Harlan. HCT116, DLD1, SW480, HT29, LS174T, and CaPan-1 cells were obtained from ATCC. HuCC-T1 cells were obtained from A. Maitra, Johns Hopkins Medical Institutions, Baltimore, Md. (Miyagiwa et al., 1989). HCT116 cells in which the p53 gene had been disrupted through homologous recombination have been previously described (Bunz et al., 1998). All cell lines were grown as monolayers in McCoy 5A medium (Gibco) supplemented with 5% fetal bovine serum at 37° C. and 5% $CO_2$.

Tumorigenicity Assays

All animal protocols were designed in accordance with the Guide for the Care and Use of Laboratory Animals (NIH Publication 86-23) and were approved by the Johns Hopkins University Institutional Animal Care and Use Committee. Six to eight week old mice were implanted subcutaneously on one flank with 3 to 6 million cancer cells. Establishment of tumors of 150 to 500 mm3 took 8 to 21 days, depending on the cell type. C. novyi-NT spores (300×106) and anti-microtubule agents were generally administered by a single intravenous injection through the tail vein in a total volume of 300 to 500 ul phosphate-buffered saline (PBS). Quantitative assessment of tumor growth was performed by measuring subcutaneous tumor grafts (major and minor axis) using electronic calipers. Tumor volume was calculated using the equation: length×width2×0.5. Progression free survival was defined as the length of time following treatment before any increase in tumor volume was observed. Mice were considered "cured" if no tumor was evident three months after treatment. Animals were weighed at least twice a week and carefully observed for signs of toxicity every day for the first week following treatment and then twice a week thereafter. At least five mice were used for each treatment arm described in the Experimental Results.

Assessment of Blood Perfusion

Mice bearing HCT116 xenografts of 300 to 500 mm3 were injected intravenously with anti-microtubule agents. At various times thereafter, they were intravenously injected with Hoechst 33342 (40 mg/kg), then euthanized two minutes later by $CO_2$ narcosis. Tumors were fixed in Tissue-Tek OTC compound (Sakura Finetek, Torrance, Calif.) and stored at −80° C. Frozen sections 10 microns in thickness were prepared with a Leica Microsystems cryostat and counterstained with acridine orange, 7.5 ug/ml, in PBS for 5 minutes. Adjacent sections were sequentially incubated with the MECA-32 monoclonal antibody (Pharmingen), a biotinylated anti-rat antibody (Jackson), and rhodamine-streptavidin (Vector). At least three sections of each of three tumors, representing middle and distal parts of the tumor, were examined under fluorescence microscopy for each agent tested, and representative results are illustrated in the figures.

Immunohistochemistry

Paraffin sections were deparaffinized, incubated with proteinase K (Invitrogen), heated at 95° C. for 20 min in citrate buffer (pH 6), and treated with peroxidase blocking reagent (Dako). Sections were incubated with a monoclonal antibody against Glucose Transporter-1 (Glut-1, Dako) followed by a biotin-conjugated secondary antibody (Pierce). A third layer consisting of HRP-conjugated anti-biotin (DAKO) was followed by diaminobenzidine (Sigma) staining. Sections were counterstained with eosin.

Quantification of *C. novyi*-NT in Tumors

Mice bearing HCT116 xenografts were treated with *C. novyi*-NT spores with or without HTI-286 (1.7 mg/kg) as described above. Following euthanasia 24-48 hr later, tumors were harvested, weighed, minced, and Dounce-homogenized. Genomic DNA was isolated using the Qiagen Genomic DNA Buffer Set and Genomic-tip 100/G. 25 ng of DNA was used in a PCR using the conditions described in (Vogelstein and Kinzler, 1999) The following primers specific for the *C. novyi*-NT phospholipase C gene were used: 5'-AAGATGGTACAGGA ACTCATTCC (SEQ ID NO:1) and 5'-GCTTGTCCGAAATACCATGTTGC (SEQ ID NO:2). No detectable primer dimers formed and no nonspecific amplification of mouse or xenograft genomic DNA occurred with these primers and PCR conditions. Real-time PCR was performed using an iCycler, and threshold cycle numbers were calculated using the iCycler Optical system interface software (Bio-Rad Lab, Hercules, Calif.). Averages of the threshold cycle number (Ct) of triplicate measurements per tumor were obtained, and three different tumors were studied for each treatment group. The results were expressed as the difference between the Ct of the treated tumor and the Ct of untreated controls, normalized to tumor weight.

Statistical Analysis

Progression-free survival across treatment groups was compared using Kaplan-Meier curves. Significance of differences was assessed using the log-rank test. Longitudinal data about tumor sizes was analyzed in two stages. First, for each animal i, we fit a regression equation of the form $\log(1+y_{it}) = a + b_i t$, where t is time and $y_{it}$ is the tumor volume of animal i at time t, relative to the tumor volume of the same animal at time 0. The p-values were determined using a student t-test on the exponential regression slope for each individual mouse. This approach was motivated by the need to account for within-animal correlations in tumor-volume measurements, as described in Section 6.3 of (Diggle P J, 1994). The fit of the animal specific regressions was generally good, with R-squared values ranging from 0.99 to 0.80.

EXAMPLE 2

Comparison of Microtubule-Interacting Chemotherapeutic Agents

The timing, route, and dose of agents are critical for the success of any experimental therapy. When two agents are combined, the number of variables that must be tested increases exponentially. To simplify interpretation of the comparisons between various anti-microtubule agents, pilot studies with representative drugs were performed. Based on the optima found through these pilots, the following protocol was implemented: (i) several doses of each chemotherapeutic agent were tested, up to a maximum of the LD50; (ii) the dose of *C. novyi*-NT was $3 \times 10^8$ spores; and (iii) the chemotherapeutic agents and bacterial spores were mixed in a total volume of 300 to 500 µl and injected intravenously. This joint administration was selected for convenience, as it was found that administration of representative chemotherapeutic agents within several hours before or after the administration of bacterial spores was as efficacious as administering the spores and drugs together.

Eighteen agents known to interact with microtubules were each tested in this manner in nude mice harboring xenografts of HCT116 human colorectal cancer cells. At least five mice harboring tumors of 150 to 500 mm3 in size were used for each experimental arm. Table 1 lists the agents tested, the doses, and the results obtained. Two classes of responses were noted. One type of response was characterized by a rapid hemorrhagic necrosis, observed only with agents that inhibited microtubule synthesis (FIG. 1A, B). The other type of response was characterized by a slow regression, observed with agents that stabilized microtubules (FIG. 2A, B). The two most promising agents from each class, based on efficacy and toxicity, were chosen for further study: these were the microtubule destabilizers HTI-286 and vinorelbine and the microtubule stabilizers docetaxel and MAC-321.

TABLE 1

Microtubule-interacting agents

| Agent | Dose* (route) | Effect alone** | Effect with *C. novyi*-NT** | Reference |
|---|---|---|---|---|
| Microtubule stabilizers | | | | |
| arsenic trioxide | 10 mg/kg × 1 (ip) | 0 | + | Griffin, 2000 |
| discodermolide | 20 mg/kg × 1 (iv) | ++ | ++++ | ter Haar, 1996 |
|  | 15 mg/kg × 1 (iv) | ++ | ++++ | |
| docetaxel | 75 mg/kg × 1 (iv) | +++ | ++++ | Rowinsky, 1997 |
|  | 50 mg/kg × 1 (iv) | ++++ | ++++ | |
|  | 25 mg/kg × 1 (iv) | ++ | +++ | |
|  | 12.5 mg/kg × 1 (iv) | + | ++ | |
| epothilone B | 25 mg/kg QD × 4 (ip) | NT | + | Bollag, 1995 |
| (+)-14-normethyldiscodermolide | 15 mg/kg × 1 (iv) | + | + | Martello, 2001 |
| paclitaxel | 30 mg/kg × 1 (iv) | 0 | + | Rowinsky, 1997 |
|  | 15 mg/kg × 1 (iv) | 0 | 0 | |
| MAC-321 | 70 mg/kg × 1 (iv) | +++ | ++++ | Sampath, 2003 |
|  | 60 mg/kg × 1 (iv) | +++ | ++++ | |
|  | 50 mg/kg × 1 (iv) | +++ | ++++ | |
|  | 45 mg/kg × 1 (iv) | +++ | ++++ | |
|  | 10 mg/kg × 1 (iv) | + | ++ | |

TABLE 1-continued

Microtubule-interacting agents

| Agent | Dose* (route) | Effect alone** | Effect with C. novyi-NT** | Reference |
|---|---|---|---|---|
| Microtubule destabilizers | | | | |
| auristatin PE | 2 mg/kg × 1 (iv) | 0 | + | Pettit, 1995 |
| auristatin PHE | 0.2 mg/kg × 1 (iv) | 0 | + | Woyke, 2001 |
| colchicine | 20 mg/kg × 1 (ip) | ++ | ++ | Baguley, 1991 |
| | 5 mg/kg × 1 (ip) | + | + | |
| | 10 mg/kg × 1 (ip) | + | + | |
| combretastatin A4P | 200 mg/kg × 1 (ip) | + | + | Tozer, 2002 |
| | 50 mg/kg × 1 (ip) | 0 | + | |
| D-24851 | 100 mg/kg × 1 (ip) | 0 | + | Bacher, 2001 |
| | 25 mg/kg × 1 (ip) | 0 | + | |
| Dolastatin 10 | 0.45 mg/kg × 1 (iv) | 0 | +++ | Chaplin, 1996 |
| | 0.30 mg/kg × 1 (iv) | 0 | +++ | |
| HTI-286 | 2.0 mg/kg × 1 (iv) | ++ | ++++ | Loganzo, 2003 |
| | 1.9 mg/kg × 1 (iv) | ++ | ++++ | |
| | 1.7 mg/kg × 1 (iv) | + | ++++ | |
| | 1.5 mg/kg × 1 (iv) | + | ++ | |
| | 1.0 mg/kg × 1 (iv) | 0 | + | |
| | 0.5 mg/kg × 1 (iv) | 0 | + | |
| noscapine | 70 mg/kg × 1 (iv) | 0 | + | Landen, 2002 |
| | 50 mg/kg × 1 (iv) | 0 | + | |
| vincristine | 10 mg/kg × 1 (ip) | 0 | + | Baguley, 1991 |
| | 5 mg/kg × 1 (ip) | 0 | 0 | |
| vinblastine | 10 mg/kg × 1 (ip) | + | + | Baguley, 1991 |
| | 5 mg/kg × 1 (ip) | 0 | 0 | |
| vinorelbine | 24 mg/kg × 1 (iv) | + | +++ | Holwell, 2001 |
| | 20 mg/kg × 1 (iv) | + | +++ | |
| | 16 mg/kg × 1 (iv) | + | ++ | |

Figure 3A:
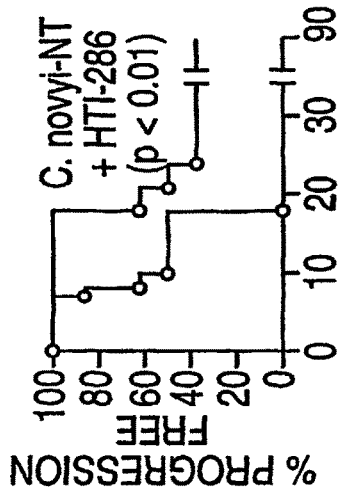
Figure 3B:
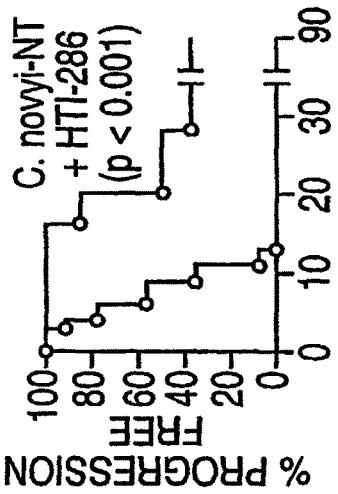

*only doses below the LD50 are shown
**NT: not tested;
0: no response;
+: inhibition of tumor growth but no tumor shrinkage;
++: 10% to 50% shrinkage in tumor volume relative to pre-treatment size;
+++: >50% shrinkage in tumor volume relative to pre-treatment size;
++++: >20% cures COBALT/HTI-286. A modest amount of hemorrhagic necrosis was observed following administration of HTI-286 to mice bearing HCT116 xenografts, but this necrosis was dramatically enhanced by co-administration of C. novyi-NT spores (FIG. 1A). This response translated into prolonged growth inhibition (FIG. 3A) and substantial increases in time to progression (FIG. 3B).

Figure 3C:
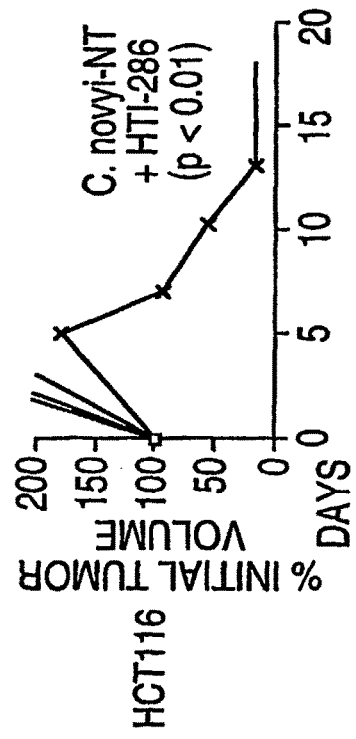
Figure 3D:
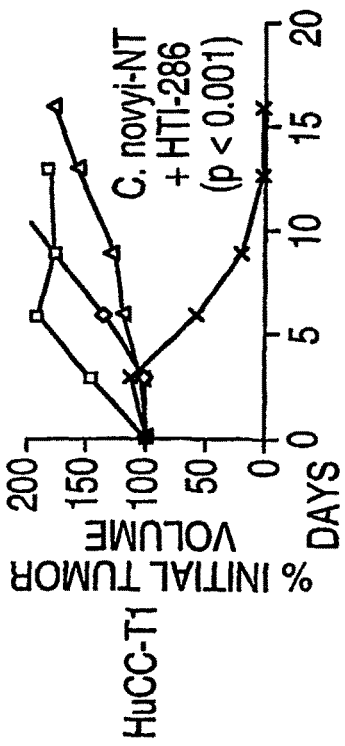
Figure 5B:
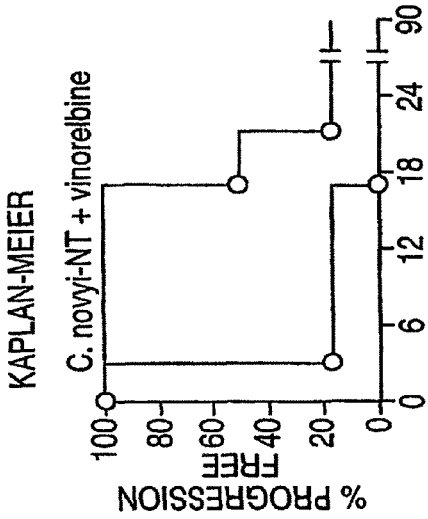
FIGS. 5A through 5D Quantification of the effects of C. novyi-NT and vinorelbine in mice bearing HCT116 or HT29 xenografts.
Animals (n>6 for each arm) were treated with vinorelbine (20 mg/kg)+/−C. novyi-NT spores. Tumor growth curves (FIGS. 5A and 5C) and progression-free survival (FIGS. 5B and 5D) are shown. Color code same as in FIGS. 3A through 3H. The p-values are based on comparisons between drug alone and drug+C. novyi-NT spores. The p-value is indicated only when the result was statistically significant.
Figure 5D:
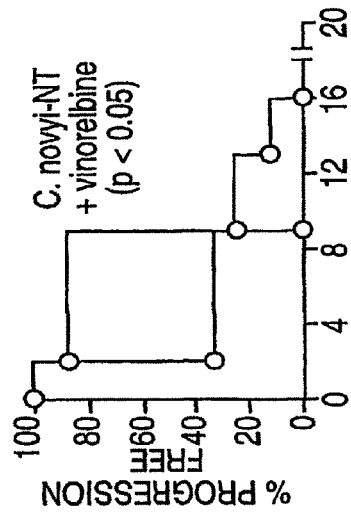
Figure 5A:
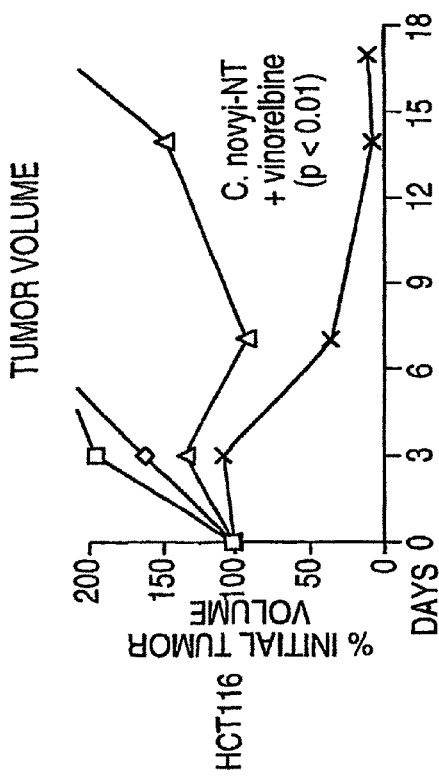
Figure 5C:
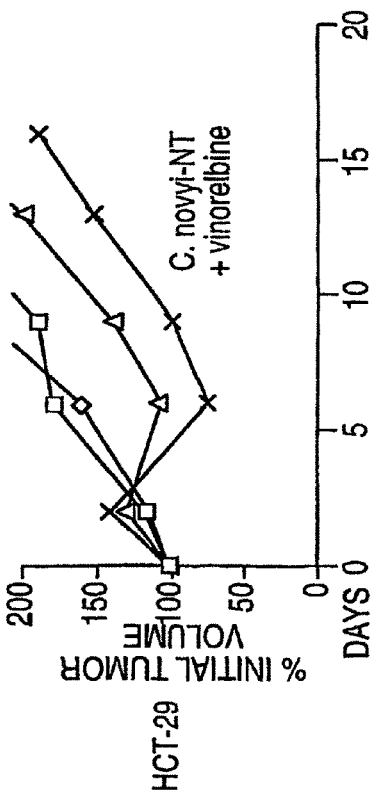

We next evaluated the responses to COBALT/HTI-286 in other murine tumor models. There was a striking similarity in the initial responses to COBALT/HTI-286 in all models tested, including the DLD1, SW480, LS174T, HT29, and HCT116-p53−/− colorectal cancers, the HuCC-T1 cholangiocarcinoma, the CaPan-1 pancreatic cancer and the B16 melanoma. All models were human tumor cell lines xenografted into nude mice with the exception of B16, which was a murine cell line transplanted into syngeneic mice. All underwent hemorrhagic necrosis within 2 or 3 days of treatment (examples in FIG. 4A to D), resulting in tumor shrinkage (examples in FIGS. 3C, E, and G). There was much more variability, however, in the responses over the long term. In some cases, such as HCT116 and HuCC-T1, approximately 40% of mice were cured by a single intravenous injection of C. novyi-NT plus HTI-286 (FIGS. 3B and D, respectively). In other cases, such as HT29 and CaPan-1, cures were observed in <10% of mice (FIGS. 3F and H). The other tumor models responded at a level intermediate to that of HCT116 and HT29. It is important to note that in all cases the addition of C. novyi-NT resulted in an improvement over the responses obtained with HTI-286 alone. It was also notable that the p53 status of tumors, which often appears to modify therapeutic effects (Pirollo et al., 2000), had little influence on the efficacy of COBALT/HTI-286. The most direct demonstration of this was provided by treatment of xenografts derived from HCT116 cells in which the p53 gene was purposefully disrupted by gene targeting (Bunz et al., 1998); the results were very similar to those shown in FIGS. 3A and B for parental HCT116 cells, with 38% of the mice cured of their p53−/− tumors.

COBALT/vinorelbine. Vinorelbine is a clinically approved drug that, like HTI-286, inhibits microtubule synthesis and thereby disrupts microtubules. Two tumor xenograft models, one (HCT116) relatively sensitive to COBALT/HTI-286 and one (HT29) relatively resistant to COBALT/HTI-286 were chosen to evaluate COBALT/vinorelbine. COBALT/vinorelbine also induced hemorrhagic necrosis, though this necrosis was less pronounced than that obtained with COBALT/HTI-286 (compare FIG. 1B with FIG. 1A). As with COBALT/HTI-286, HCT116 responded much better to COBALT/vinorelbine than did HT29 (FIG. 5).

Figure 2B:
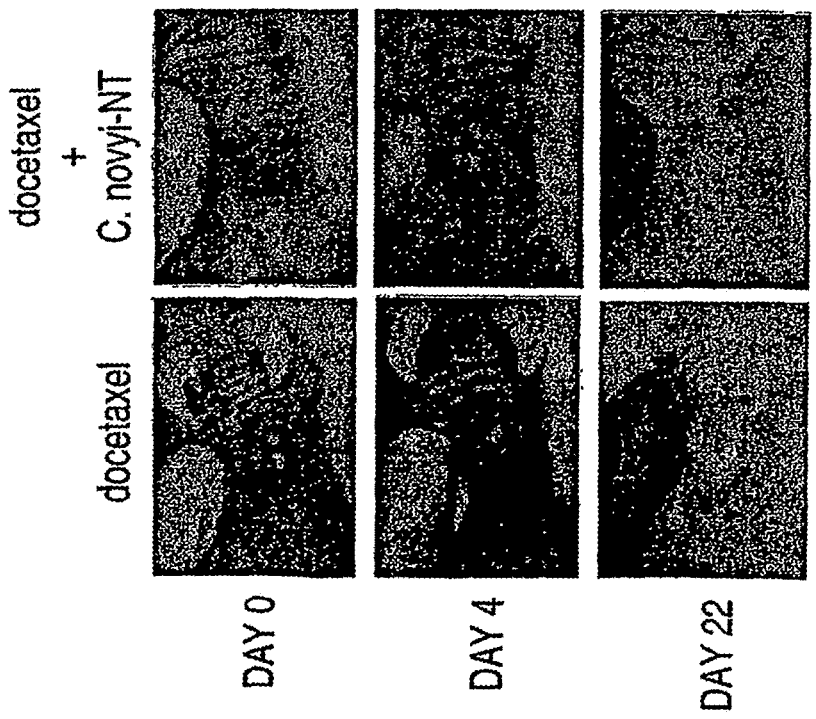
Figure 6A:
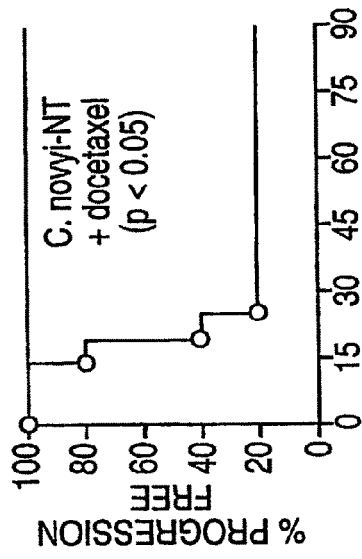
FIGS. 6A through 6F Quantification of the effects of C. novyi-NT and docetaxel in mice bearing various xenografts. Animals (n>5 for each arm) were treated with docetaxel+/−C. novyi-NT. The dose of docetaxel (50 to 75 mg/kg) was optimized for each xenograft type; for example, HT29 was less sensitive to docetaxel than the other tumor types. Tumor growth curves (FIGS. 6A, 6C and 6E) and progression free survival (Kaplan-Meier plots, FIGS. 6B, 6D and 6F) are shown. Color code same as in FIGS. 3A through 3H. The p-values are based on comparisons between drug alone and drug+*C. novyi*-NT spores. The p-value is indicated only when the result was statistically significant.
Figure 6B:
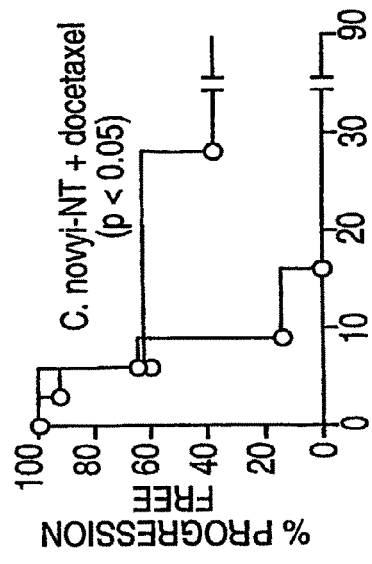
Figure 6C:
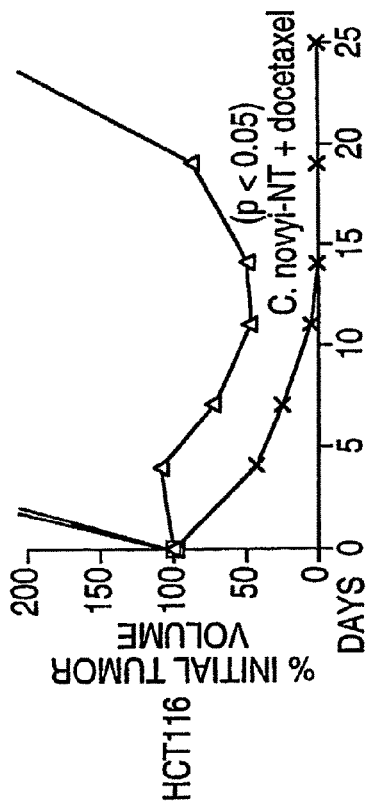
Figure 6D:
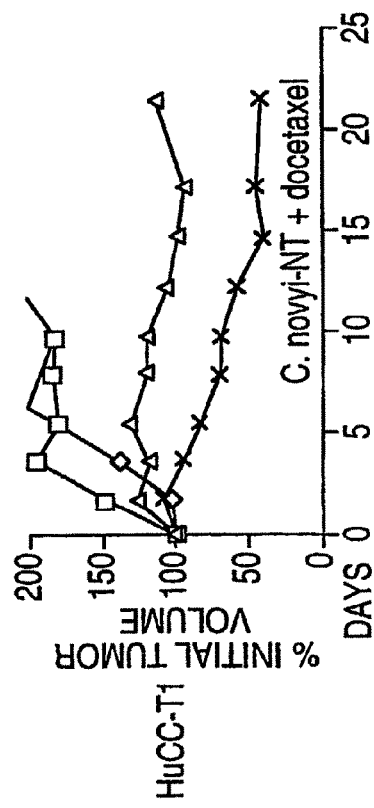
Figure 6F:
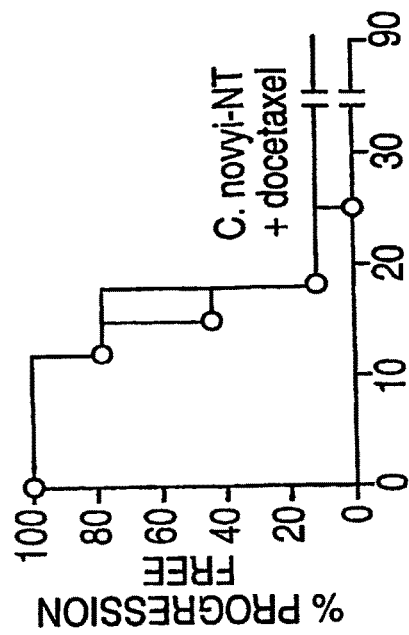
Figure 6E:
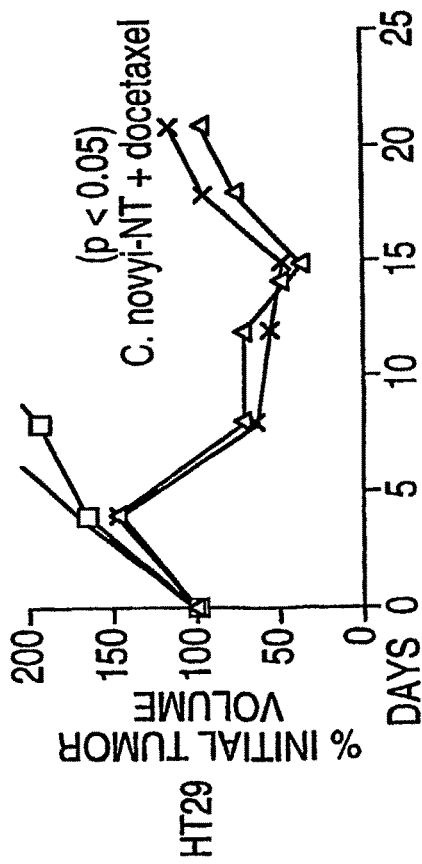

COBALT/docetaxel and COBALT/MAC-321. As noted above, a very different type of response was observed with C. novyi-NT when used in combination with microtubule stabilizing drugs, exemplified by docetaxel and MAC-321. In particular, there was a much slower response and no hemorrhagic necrosis following COBALT with these agents (FIG. 2). Additionally, the tumors generally underwent a more pronounced regression with docetaxel or MAC-321 alone than with HTI-286 or vinorelbine alone. Nevertheless, the addition of C. novyi-NT spores substantially improved the durations of the remissions achieved with these agents. All mice bearing HCT116 xenografts treated with COBALT/docetaxel were cured, unlike the case with docetaxel alone (FIG. 6A, B). The responses of mice bearing HuCC-T1 were also encouraging (FIG. 6 C, D). Like the case with COBALT/HTI-286, HT29 did not respond nearly as well as the other two tumor types tested (FIG. 6E, F). HCT116 cells with genetically disrupted p53 genes also responded to COBALT/docetaxel, with complete regressions in all mice and cures in 44%, whereas docetaxel alone cured only 13% of the mice.

Figure 7B:
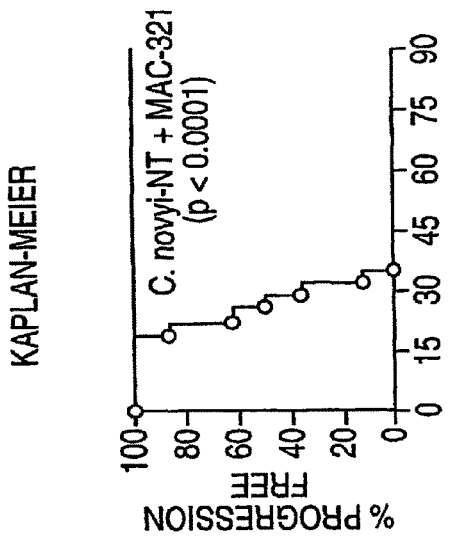
Figure 7D:
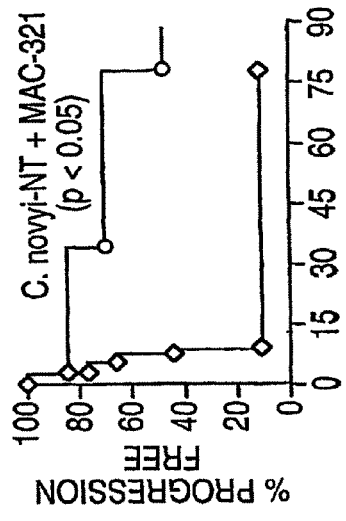
Figure 7A:
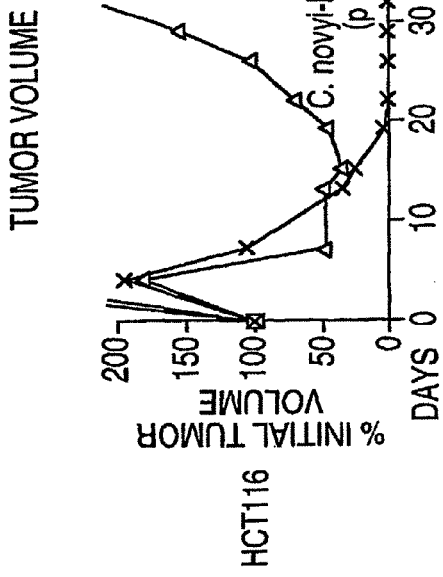
Figure 7C:
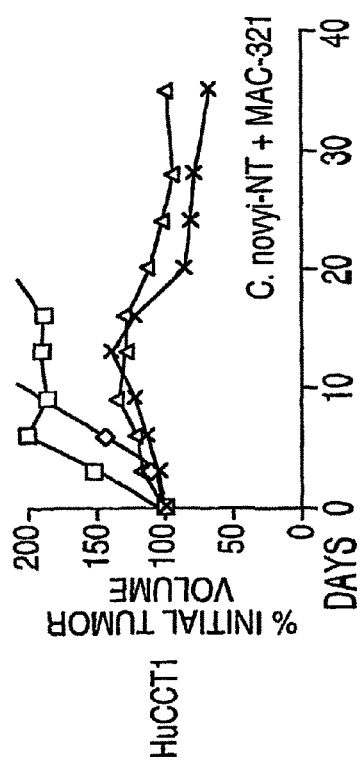

The responses of HCT116 tumors to COBALT/MAC-321 were very similar to those of COBALT/docetaxel, as would have been predicted from their structural similarity. The three xenograft types tested underwent major regressions, with cures achieved in a substantial fraction of two of them (FIG. 7). Though the initial tumor regressions were no more impressive with MAC-321 plus *C. novyi*-NT than with MAC-321 alone, the duration of the responses was markedly different when *C. novyi*-NT was added. Four of seven mice harboring HuCC-T1 xenografts were cured following *C. novyi*-NT plus MAC-321 treatment, whereas only one of eight mice treated with MAC-321 alone was cured ($p<0.05$; FIG. 7D). Similarly, all mice bearing HCT116 xenografts were cured following COBALT/MAC-321 while no mice treated with the MAC-321 alone were cured ($p<0.0001$ FIG. 7B).

EXAMPLE 3

Mechanisms Underlying the Two Classes of Responses

Figure 8:
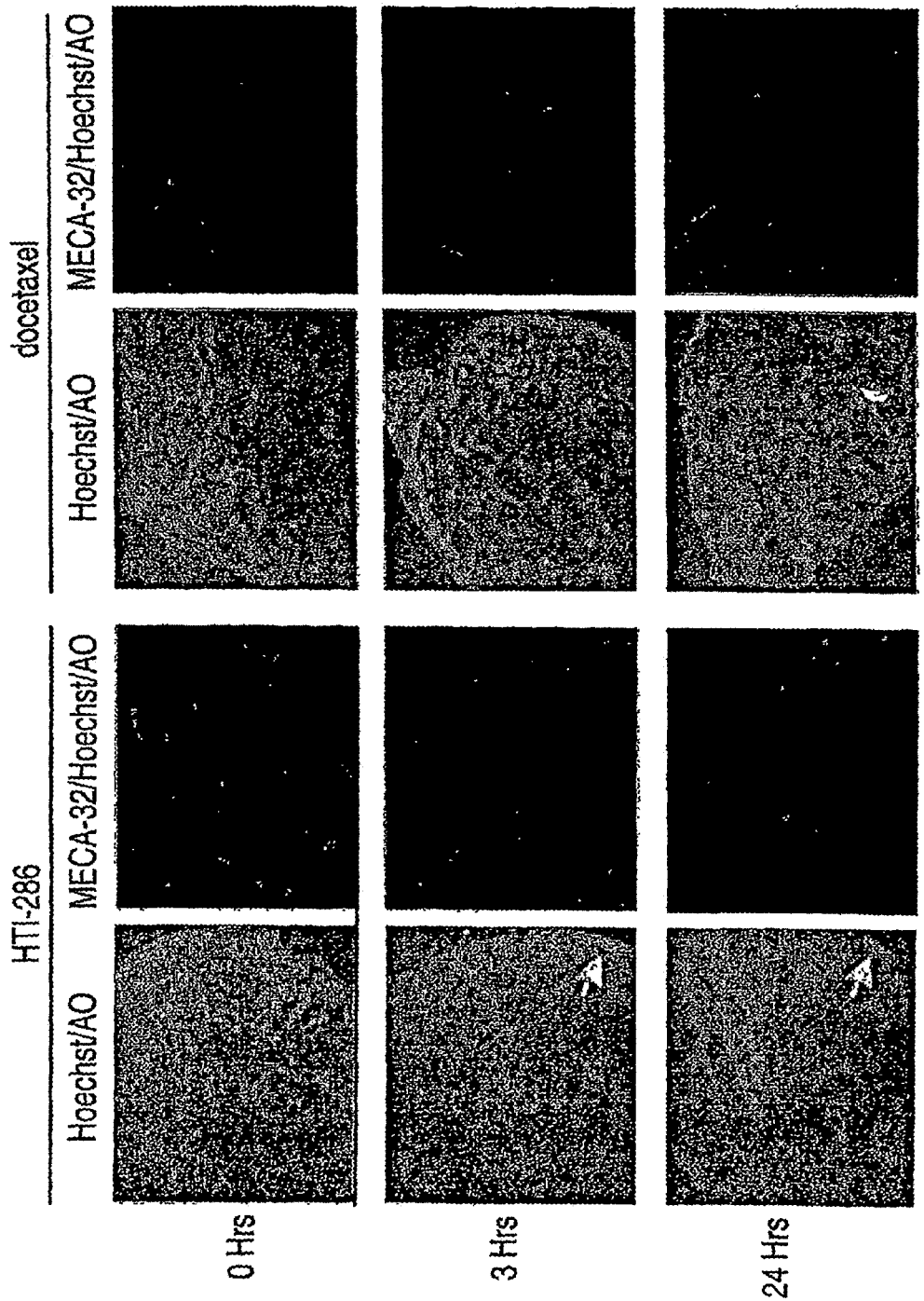
FIG. 8 Effect of docetaxel and HTI-286 on blood flow. Mice bearing subcutaneous xenografts of HCT116 cells, 400-500 mm3 in size, were intravenously injected with HTI-286 (1.7 mg/kg) or docetaxel (50 mg/kg). Three or 24 hours after treatment, mice were intravenously injected with Hoechst 33342 (40 mg/kg) and euthanized two minutes later. Tumors were cryosectioned and viewed by fluorescence microscopy after counter-staining with acridine orange (AO). Endothelial cells are stained blue when they have taken up the Hoechst 33342 dye. Adjacent sections were stained with MECA-32 monoclonal antibody, a vascular endothelium-specific marker. Arrows point towards normal blood vessels unaffected by HTI-286 treatment in overlying skin.

We sought to determine the basis for the differences in responses observed with the two classes of microtubule-interacting drugs, represented by HTI-286 and docetaxel, when used in conjunction with *C. novyi*-NT. It has previously been shown that some microtubule-interacting drugs, particularly those that inhibit microtubule synthesis such as DMXAA and combretastatin A4P, inhibit tumor blood flow (Baguley, 2003) (Tozer et al., 2002). To test whether HTI-286 and docetaxel affected blood flow, we treated HCT116 tumor-bearing mice with these drugs, then intravenously injected the cell-permeable DNA-binding dye Hoechst 33342 two minutes prior to sacrifice. Hoechst predominantly labels the nuclei of endothelial cells in such experiments, as the dye does not have time to diffuse through the tissue during the interval between injection and sacrifice (Bernsen et al., 1999). Frozen sections of the tumors revealed that blood flow to the tumors was almost completely inhibited by HTI-286, a microtubule destabilizer, by 3 hr and that this inhibition remained for at least 24 hr (FIG. 8). In contrast, docetaxel, a microtubule stabilizer, had no observable effects on blood flow (FIG. 8). The effect of HTI-286 on blood flow was tumor-specific in that Hoechst staining of the blood vessels in the skin overlying the tumors was not affected (e.g., arrows in 3 and 24 hr time points in FIG. 8). Staining adjacent sections with the endothelial specific antibody MECA32 revealed that endothelial cells were still present after treatment with HTI-286 but they were not being perfused with the Hoechst dye dissolved in the blood. Many of them looked abnormal, with few of the long continuous vessels that were evident in controls or in animals treated with docetaxel.

These results suggested that treatment with microtubule destabilizers increased the extent of hypoxia within tumors by inhibiting blood flow, thereby creating a larger niche for the anaerobic bacteria to populate. Two independent tests of this hypothesis were performed. First, we directly assessed hypoxia within tumors by staining with an antibody to Glucose Transporter-1 (Glut-1). Glut-1 has been extensively studied and shown to be specifically expressed only in hypoxic regions (Airley et al., 2001). Tumors treated with HTI-286 expressed large amounts of Glut-1 within 6 hr of treatment (FIG. 9E). Small lakes of erythrocytes, indicating static blood flow, were observed in adjacent sections, and no evidence of tumor cell death was observed at these early time points after HTI-286 treatment (FIG. 9B). No increase of Glut-1 staining was found in tumors treated with docetaxel (FIG. 9F) compared to untreated tumors (FIG. 9D).

Second, we directly tested the size of bacterial populations within tumors by measuring the number of bacteria at various times following intravenous injection of *C. novyi*-NT spores into mice bearing HCT116 xenografts. Because of the exquisite sensitivity of these bacteria to oxygen, it was difficult to reliably assess the number of bacteria in tumors through conventional microbiologic evaluation, and we chose to use quantitative PCR methods for this purpose. Using primers specific for the phospholipase C gene of *C. novyi*-NT (Tsutsui et al., 1995), we found that these bacteria accumulated to a level of $4.8 \times 10^8$ bacteria per gram of tumor (range 2.2 to $8.1 \times 10^8$) after 24 hours when administered without chemotherapeutic drugs. When co-injected with HTI-286, the number of bacteria increased by 6.8-fold+/−0.08 (standard deviation). In contrast, when co-administered with docetaxel, the number of bacteria increased by only 1.6-fold+/−0.3 (standard deviation).

EXAMPLE 4

Lowering the Dose of Microtubule Destabilizers

Figures 10E, 10F:
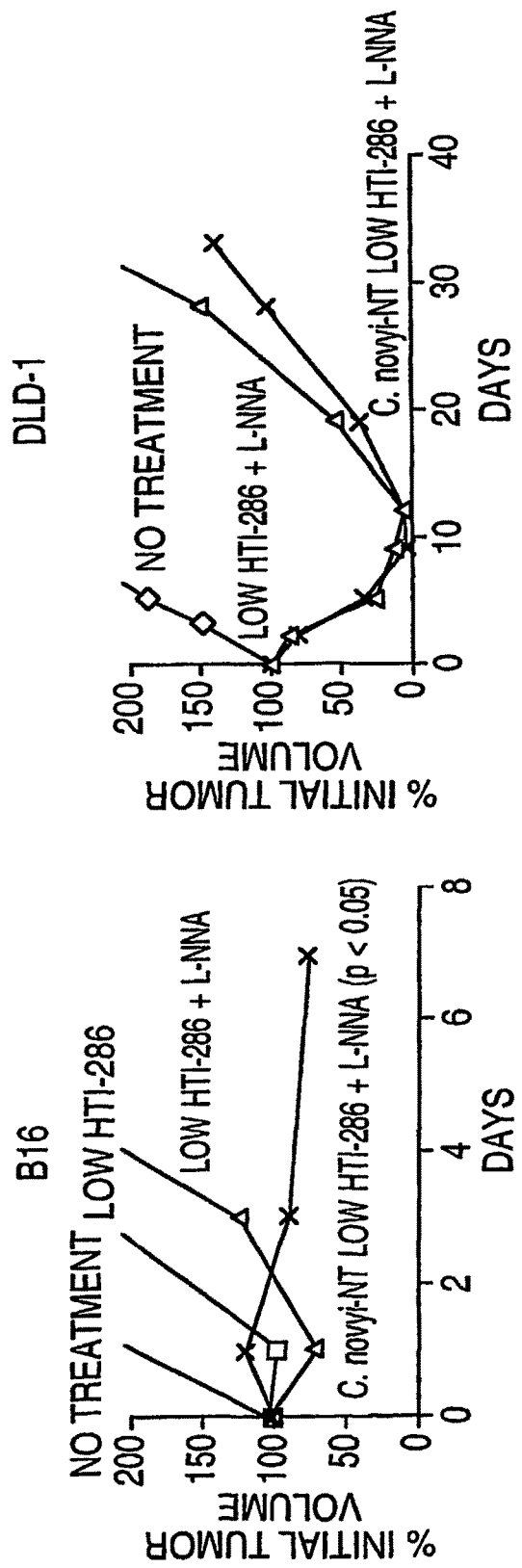
Figure 11:
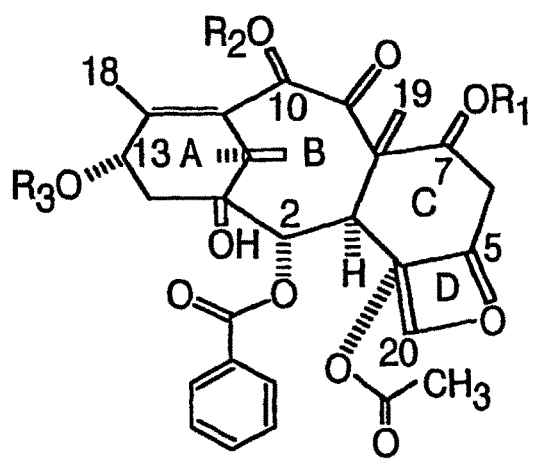
FIG. 11 Chemical structures of paclitaxel, docetaxcel, and MAC-321.

Clinical trials of microtubule destabilizers have often been disappointing in that the maximum tolerated dose (MTD) was reached before any anti-vascular effects were observed. A recent study has shown that the dose of the microtubule destabilizers combretastatin A4P could be reduced when nitric oxide synthesis (NOS) inhibitors were concurrently administered (Parkins et al., 2000). This strategy was based on the observation that the vascular relaxing compound NO is released from some tumor cells in the presence of vascular injury and could thereby combating the effects of the combretastatin A4P on tumor blood flow (Parkins et al., 2000). In view of the anti-vascular action of HTI-286 described above, we tested whether this concept could be applied to treatment with HTI-286. We administered a well-tolerated dose of the NOS inhibitor L-NNA together with varying doses of HTI-286 to mice bearing HCT116 xenografts. We found that L-NNA added little to the effects observed with either *C. novyi*-NT alone or high doses of HTI-286 plus *C. novyi*-NT, when vascular shut-down was already complete. However, L-NNA significantly enhanced the responses to low doses of HTI-286 without adding toxicity. The response was enhanced further when L-NNA and low doses of HTI-286 were used in combination with *C. novyi*-NT (FIG. 10A). Marked hemorrhagic necrosis was observed, similar to that shown in FIG. 1, while little hemorrhagic necrosis was observed when any one of the three components (L-NNA, HTI-286 at 1 mg/kg, or *C. novyi*-NT spores) were left out. *C. novyi*-NT was able to substantially improve the therapeutic effects of treatment with L-NNA plus low doses of HTI-286 in HuCC-T1, SW480, and B16 tumors, but had only small effects in HT29 and DLD-1 cells (examples in FIG. 10B-F).

EXAMPLE 5

Toxicity of COBALT

In our previous study of *C. novyi*-NT plus dolastatin-10 and mitomycin C, toxicity was of particular concern, as up to 30% of the mice with tumors died from the treatment. This toxicity was observed only when the combination of *C. novyi*-NT spores and the drugs was administered and not with either the bacteria or the drugs alone. The new combinations described in the current study proved to be significantly less toxic. A total of >600 nude mice bearing relatively large xenografts were treated with C. novyi-NT in combination with HTI-286, vinorelbine, docetaxel, or MAC-321. Though major tumor regressions were common, few mice died as a result of therapy (Table 2) No deaths occurred after treatment with the microtubule stabilizers plus C. novyi-NT, while 4% to 8% of mice treated with microtubule destabilizers plus C. novyi-NT died. The only other toxicity observed was transient weight loss (Table 3). Mice treated with the drugs alone lost ~5 to 10% of their body weight within 7 days, while weight loss after treatment with C. novyi-NT plus these drugs varied from 8% to 18%. All weights recovered to pre-treatment levels within two weeks.

TABLE 2

Mortality following COBALT

| Treatment | Drug dose (mg/kg) | # mice | # dead (%)* |
|---|---|---|---|
| No treatment control | — | 110 | 0 |
| C. novyi-NT spores | — | 118 | 0 |
| docetaxel | 25.0 | 5 | 0 |
|  | 50.0 | 43 | 0 |
|  | 75.0 | 34 | 0 |
| C. novyi-NT + docetaxel | 25.0 | 5 | 0 |
|  | 50.0 | 45 | 0 |
|  | 75.0 | 33 | 0 |
| MAC-321 | 45.0 | 28 | 0 |
|  | 50.0 | 9 | 0 |
|  | 60.0 | 23 | 0 |
|  | 70.0 | 9 | 0 |
| C. novyi-NT + MAC-321 | 45.0 | 32 | 0 |
|  | 50.0 | 9 | 0 |
|  | 60.0 | 23 | 0 |
|  | 70.0 | 9 | 0 |
| vinorelbine | 16.0 | 16 | 0 |
|  | 20.0 | 12 | 0 |
|  | 24.0 | 12 | 0 |
| C. novyi-NT + vinorelbine | 16.0 | 26 | 0 |
|  | 20.0 | 15 | 1 (6.7%) |
|  | 24.0 | 12 | 0 |
| HTI-286 | 1.7 | 104 | 3 (2.9%) |
|  | 1.9 | 55 | 3 (5.4%) |
|  | 2.0 | 47 | 5 (10.6%) |
| C. novyi-NT + HTI-286 | 1.7 | 127 | 10 (7.9%) |
|  | 1.9 | 98 | 4 (4.1%) |
|  | 2.0 | 188 | 8 (4.3%) |

*Treatment-related deaths (i.e., those that occurred within one week of the initiation of therapy) were determined from experiments with HCT116, HT29, DLD1, SW480, Capan-1 and HuCC-T1 xenografts.

TABLE 3

Weight loss after COBALT

| Treatment | Drug dose (mg/kg) | # mice | Weight Loss (%)* |
|---|---|---|---|
| No treatment control | — | 39 | 0.0 |
| C. novyi-NT spores | — | 8 | 5.5 |
| docetaxel | 50.0 | 8 | 11.0 |
| C. novyi-NT + docetaxel | 50.0 | 9 | 12.0 |
| MAC-321 | 60.0 | 8 | 5.5 |
| C. novyi-NT + MAC-321 | 60.0 | 7 | 10.2 |
| vinorelbine | 24.0 | 6 | 8.3 |
| C. novyi-NT + vinorelbine | 24.0 | 6 | 8.3 |
| HTI-286 | 1.7 | 6 | 11.4 |
| C. novyi-NT + HTI-286 | 1.7 | 6 | 18.3 |

*Weight loss was determined from experiments with HCT116 xenografts. The maximum average weight loss relative to the weight one day prior to treatment is indicated.

The results described above show that C. novyi-NT, when combined with specific microtubule-interacting drugs, can have dramatic effects on experimental tumors. Hemorrhagic necrosis following COBALT/microtubule destabilizers was observed in all nine tumor models tested. C. novyi-NT was also found to cooperate with microtubule stabilizing agents, converting the transient tumor regressions obtained with the drugs alone to cures in the most sensitive models. It was notable that these responses were observed after only a single dose of C. novyi-NT spores plus drugs.

Several intriguing questions are raised by these data. The first relates to the markedly different effects of microtubule stabilizers and microtubule destabilizers. Microtubule stabilizers like docetaxel and MAC-321 had substantial anti-tumor effects on their own, but rarely produced cures when administered only once. From the results presented in this paper, we surmise that these drugs leave foci of tumor cells in poorly perfused regions of the tumors, either because adequate concentrations of drugs are not reached in these regions or because the tumor cells there are not replicating and are therefore not as susceptible to the cytocidal activities of these agents. Because C. novyi-NT specifically targets the hypoxic areas least likely to be killed by these agents, it is not surprising that the spores can cooperate with them. Though delivery of spores to the poorly perfused areas of tumors may be relatively low, it presumably only requires one or a few spores to reach such areas. With a doubling time of 45 minutes, the C. novyi-NT can rapidly proliferate, and as shown previously (Dang et al., 2001), the germinated bacteria have the capacity to kill surrounding tumor cells, stopping only when they reach the well-oxygenated regions.

In contrast, microtubule destabilizers appear to disrupt blood flow within the tumors, presumably because the microtubule networks in vascular endothelial cells or perivascular smooth muscle cells are specifically sensitive to such disruption (Griggs et al., 2001). Though the basis for this differential sensitivity is not understood, it is clear that many microtubule destabilizing agents have similar effects on tumor vasculature, rapidly stopping blood flow to the tumor (Griggs et al., 2001). HTI-286 is a novel anti-microtubule destabilizer that binds α-tubulin at the vinca-peptide binding site, unlike classic agents such as colchicine or combretastatin A4 (Hamel and Covell, 2002). Because HTI-286 stops blood flow without destroying endothelial cells, much like these previously studied agents, it is clear that the disruption of microtubules per se, rather than the way in which the drug binds to microtubules, is critical for this activity. Based on these observations, we conclude that the efficacy of COBALT/HTI-286 is in part due to the ability of the drugs to decrease blood flow and thereby create larger regions of hypoxia for the spores to germinate and multiply. This conclusion is consistent with the demonstration that there were far greater numbers of bacteria in tumors treated with COBALT/HTI-286 than with C. novyi-NT alone.

Several other practical points emerged from our study. Toxicity is always a serious issue when dealing with biologic agents that are capable of self-replicating. In our initial studies with C. novyi-NT, both dolastatin-10 and mitomycin C were required to achieve pronounced effects, and this triple combination was toxic, killing up to a third of the animals (Dang et al., 2001). The new combinations, generally employing only a single agent in combination with C. novyi-NT, had acceptable toxicities (Tables 2 and 3). Importantly, no deaths were observed in animals treated with C. novyi-NT alone, COBALT/docetaxel or COBALT/MAC-321 (Table 2), despite the substantial cure rates achieved when using either combination (FIGS. 6, 7). The basis for the small number of deaths that occurred after COBALT/HTI-286 or COBALT/vinorelbine is unclear. Deaths were a bit more common in very large tumors (>650 mm3) than in tumors of small or intermediate size. This suggests that tumor lysis syndrome, sepsis, or release of toxic products from the tumors plays a role in the toxicity of COBALT/HTI-286, each of which can be expected to be greater in larger tumors. Detailed necropsy studies of animals that died after COBALT/HTI-286 have not revealed any specific abnormalities that would point to a specific cause of death.

Another issue that has been raised with regard to anaerobic bacteriolytic therapies concerns the size of tumors that can be successfully treated. Smaller tumors are expected to have a smaller fraction of necrosis and hypoxia, thereby limiting the potential of anaerobic bacteria to proliferate. The results obtained in the current study suggest that this may not be as much of a problem as anticipated. Though reduced efficacy was observed with HCT116 tumors of <100 mm3 in size compared to larger tumors, complete regressions were achieved with tumors as small as 100 mm3, 250 mm3 and 150 mm3 after COBALT/HTI-286, COBALT/docetaxel, and COBALT/MAC-321, respectively, while such regressions were not seen after administration of the same drugs in the absence of C. novyi-NT spores.

There were other encouraging findings in this study that may be applicable to the planning of future clinical trials. The effective dose range of C. novyi-NT was very wide. Though we chose to administer 3×108 spores per mouse, we found that 100-fold lower doses (3×106) induced >90% shrinkage of HCT116 tumors when given together with the standard dose of HTI-286 (unpublished data). The relatively low toxicity and the ability of C. novyi-NT spores to enhance the effects of several anti-microtubule agents with different mechanisms of action in several different tumor models also bodes well for future clinical application.

REFERENCES

Airley, R., Loncaster, J., Davidson, S., Bromley, M., Roberts, S., Patterson, A., Hunter, R., Stratford, I., and West, C. (2001). Glucose transporter glut-1 expression correlates with tumor hypoxia and predicts metastasis-free survival in advanced carcinoma of the cervix. Clin Cancer Res 7, 928-934.

Altmann, K. H. (2003). Epothilone B and its analogs—a new family of anticancer agents. Mini Rev Med Chem 3, 149-158.

Bacher, G., Nickel, B., Emig, P., Vanhoefer, U., Seeber, S., Shandra, A., Klenner, T., and Beckers, T. (2001). D-24851, a novel synthetic microtubule inhibitor, exerts curative antitumoral activity in vivo, shows efficacy toward multi-drug-resistant tumor cells, and lacks neurotoxicity. Cancer Res 61, 392-399.

Baguley, B. C. (2003). Antivascular therapy of cancer: DMXAA. Lancet Oncol 4, 141-148.

Baguley, B. C., Holdaway, K. M., Thomsen, L. L., Zhuang, L., and Zwi, L. J. (1991). Inhibition of growth of colon 38 adenocarcinoma by vinblastine and colchicine: evidence for a vascular mechanism. Eur J Cancer 27, 482-487.

Bernsen, H. J., Rijken, P. F., Hagemeier, N. E., and van der Kogel, A. J. (1999). A quantitative analysis of vascularization and perfusion of human glioma xenografts at different implantation sites. Microvasc Res 57, 244-257.

Bollag, D. M., McQueney, P. A., Zhu, J., Hensens, O., Koupal, L., Liesch, J., Goetz, M., Lazarides, E., and Woods, C. M. (1995). Epothilones, a new class of micro-tubule-stabilizing agents with a taxol-like mechanism of action. Cancer Res 55, 2325-2333.

Brown, J. M. (2002). Tumor microenvironment and the response to anticancer therapy. Cancer Biol Ther 1, 453-458.

Brown, J. M., and Giaccia, A. J. (1998). The unique physiology of solid tumors: opportunities (and problems) for cancer therapy. Cancer Res 58, 1408-1416.

Bunz, F., Dutriaux, A., Lengauer, C., Waldman, T., Zhou, S., Brown, J. P., Sedivy, J. M., Kinzler, K. W., and Vogelstein, B. (1998). Requirement for p53 and p21 to sustain G2 arrest after DNA damage. Science 282, 1497-1501.

Chaplin, D. J., Pettit, G. R., Parkins, C. S., and Hill, S. A. (1996). Antivascular approaches to solid tumour therapy: evaluation of tubulin binding agents. Br J Cancer Suppl 27, S86-88.

Chen, J. G., and Horwitz, S. B. (2002). Differential mitotic responses to microtubule-stabilizing and -destabilizing drugs. Cancer Res 62, 1935-1938.

Dang, L. H. Bettegowda, C. M, Huso, D. L., Kinzler, K. W., and Vogelstein, B. (2001) Combination bacteriolytic therapy for the treatment of experimental tumors. Proc Natl Acad Sci USA. 98: 15155-15160.

Diggle P J, L. K.-Y., Zeger S L (1994). Analysis of Longitudinal Data, Oxford University Press).

Folkman, J. (2002). Role of angiogenesis in tumor growth and metastasis. Semin Oncol 29, 15-18.

Griffin, R. J., Lee, S. H., Rood, K. L., Stewart, M. J., Lyons, J. C., Lew, Y. S., Park, H., and Song, C. W. (2000). Use of arsenic trioxide as an antivascular and thermosensitizing agent in solid tumors. Neoplasia 2, 555-560.

Griggs, J., Metcalfe, J. C., and Hesketh, R. (2001). Targeting tumour vasculature: the development of combretastatin A4. Lancet Oncol 2, 82-87.

Hamel, E., and Covell, D. G. (2002). Antimitotic peptides and depsipeptides. Curr Med Chem Anti-Canc Agents 2, 19-53.

Heppner, F., and Mose, J. R. (1978). The liquefaction (oncolysis) of malignant gliomas by a non pathogenic Clostridium. Acta Neurochir (Wien) 42, 123-125.

Jain, R. K., and Forbes, N. S. (2001). Can engineered bacteria help control cancer? Proc Natl Acad Sci USA 98, 14748-14750.

Kerbel, R. S. (2000). Tumor angiogenesis: past, present and the near future. Carcinogenesis 21, 505-515.

Landen, J. W., Lang, R., McMahon, S. J., Rusan, N. M., Yvon, A. M., Adams, A. W., Sorcinelli, M. D., Campbell, R., Bonaccorsi, P., Ansel, J. C., et al. (2002). Noscapine alters microtubule dynamics in living cells and inhibits the progression of melanoma. Cancer Res 62, 4109-4114.

Liu, S. C., Minton, N. P., Giaccia, A. J., and Brown, J. M. (2002). Anticancer efficacy of systemically delivered anaerobic bacteria as gene therapy vectors targeting tumor hypoxia/necrosis. Gene Ther 9, 291-296.

Loganzo, F., Discafani, C. M., Annable, T., Beyer, C., Musto, S., Hari, M., Tan, X., Hardy, C., Hernandez, R., Baxter, M., et al. (2003). HTI-286, a synthetic analogue of the tripeptide hemiasterlin, is a potent antimicrotubule agent that circumvents P-glycoprotein-mediated resistance in vitro and in vivo. Cancer Res 63, 1838-1845.

Low, K. B., Ittensohn, M., Le, T., Platt, J., Sodi, S., Amoss, M., Ash, O., Carmichael, E., Chakraborty, A., Fischer, J., et al. (1999). Lipid A mutant Salmonella with suppressed virulence and TNFalpha induction retain tumor-targeting in vivo. Nat Biotechnol 17, 37-41.

Martello, L. A., LaMarche, M. J., He, L., Beauchamp, T. J., Smith, A. B., and Horwitz, S. B. (2001). The relationship between Taxol and (+)-discodermolide: synthetic analogs and modeling studies. Chem Biol 8, 843-855.

Miyagiwa, M., Ichida, T., Tokiwa, T., Sato, J., and Sasaki, H. (1989). A new human cholangiocellular carcinoma cell line (HuCC-T1) producing carbohydrate antigen 19/9 in serum-free medium. In Vitro Cell Dev Biol 25, 503-510.

Parkins, C. S., Holder, A. L., Hill, S. A., Chaplin, D. J., and Tozer, G. M. (2000). Determinants of anti-vascular action by combretastatin A-4 phosphate: role of nitric oxide. Br J Cancer 83, 811-816.

Pettit, G. R. (1997). The dolastatins. Fortschr Chem Org Naturst 70, 1-79. Pettit, G. R., Srirangam, J. K., Barkoczy, J., Williams, M. D., Durkin, K. P., Boyd, M. R., Bai, R., Hamel, E., Schmidt, J. M., and Chapuis, J. C. (1995). Antineoplastic agents 337. Synthesis of dolastatin 10 structural modifications. Anticancer Drug Des 10, 529-544.

Pirollo, K. F., Bouker, K. B., and Chang, E. H. (2000). Does p53 status influence tumor response to anticancer therapies? Anticancer Drugs 11, 419-432.

Rowinsky, E. K. (1997). The development and clinical utility of the taxane class of antimicrotubule chemotherapy agents. Annu Rev Med 48, 353-374.

Sampath, D., Discafani, C. M., Loganzo, F., Beyer, C., Liu, H., Tan, X., Musto, S., and Annable, T., Gallagher, P., Rios, C., Greenberger, L. M. (2003). MAC-321, a novel taxane with greater efficacy than paclitaxel and docetaxel in vitro and in vivo. Mol Cancer Ther, in press.

Smith, I. A., Kaufman, M. D., Beachamp, T. J., LaMarche, M. J., and Arimoto, H. (2000). Gram-Scale Synthesis of (+)-Discodermolide. Org Lett 2, 1983.

ter Haar, E., Kowalski, R. J., Hamel, E., Lin, C. M., Longley, R. E., Gunasekera, S. P., Rosenkranz, H. S., and Day, B. W. (1996). Discodermolide, a cytotoxic marine agent that stabilizes microtubules more potently than taxol. Biochemistry 35, 243-250.

Tozer, G. M., Kanthou, C., Parkins, C. S., and Hill, S. A. (2002). The biology of the combretastatins as tumour vascular targeting agents. Int J Exp Pathol 83, 21-38.

Tsutsui, K., Minami, J., Matsushita, O., Katayama, S., Taniguchi, Y., Nakamura, S., Nishioka, M., and Okabe, A. (1995). Phylogenetic analysis of phospholipase C genes from *Clostridium perfringens* types A to E and *Clostridium novyi*. J Bacteriol 177, 7164-7170.

Vogelstein, B., and Kinzler, K. W. (1999). Digital PCR. Proc Natl Acad Sci USA 96, 9236-9241.

Woyke, T., Pettit, G. R., Winkelmann, G., and Pettit, R. K. (2001). In vitro activities and postantifungal effects of the potent dolastatin 10 derivative auristatin PHE. Antimicrob Agents Chemother 45, 3580-3584.

The invention claimed is:

1. A method for treating tumors in a pet mammal comprising:
    administering to the pet mammal spores of toxin-defective *Clostridium novyi*; and
    administering to the mammal a microtubule stabilizing anti-tumor agent; whereby the tumor regresses or its growth is slowed or arrested.

2. The method of claim 1 wherein the pet mammal is a dog.

3. The method of claim 1 wherein the pet mammal is a cat.

4. A method for treating tumors in an agricultural mammal comprising:
    administering to the agricultural mammal spores of toxin-defective *Clostridium novyi*; and
    administering to the mammal a microtubule stabilizing anti-tumor agent;
    whereby the tumor regresses or its growth is slowed or arrested.

5. The method of claim 4 wherein the agricultural mammal is selected from the group consisting of cows, sheep, horses, goats, and pigs.

6. A method for treating tumors in a laboratory mammal comprising:
    administering to the laboratory mammal spores of a toxin-defective *Clostridium novyi*; and
    administering to the mammal a microtubule stabilizing anti-tumor agent; whereby the tumor regresses or its growth is slowed or arrested.

7. The method of claim 6 wherein the laboratory mammal is selected from the group consisting of rats, hamsters, monkeys, mice, and rabbits.

8. A method for treating tumors in a human, comprising:
    administering to the human spores of a toxin-defective *Clostridium novyi*; and
    administering to the human a microtubule stabilizing anti-tumor agent;
    whereby the tumor regresses or its growth is slowed or arrested.

9. The method of claim 1, 4, 6, or 8 wherein the spores are administered intravenously.

10. The method of claim 1, 4, 6, or 8 wherein the spores are administered intratumorally.

SEQUENCE LISTING

```
<160> NUMBER OF SEQ ID NOS: 2

<210> SEQ ID NO 1
<211> LENGTH: 23
<212> TYPE: DNA
<213> ORGANISM: Clostridium novyi

<400> SEQUENCE: 1
aagatggtac aggaactcat tcc                                             23

<210> SEQ ID NO 2
<211> LENGTH: 23
<212> TYPE: DNA
<213> ORGANISM: Clostridium novyi

<400> SEQUENCE: 2
gcttgtccga aataccatgt tgc                                             23
```

11. The method of claim 1, 4, 6, or 8 wherein all or part of a toxin gene of a wild type form of the anaerobic bacterium is deleted.

12. The method of claim 2 or 8 wherein the microtubule stabilizing anti-tumor agent is a taxane.

13. The method of claim 2 or 8 wherein the microtubule stabilizing anti-tumor agent is selected from the group consisting of 10-deacetyltaxol; 7-epi-10-deacetyltaxol; 7-xylosyl-10-deacetyltaxol; 7-epi-taxol; cephalomannine; baccatin III; baccatin V; 10-deacetylbaccatin III; 7-epi-10-deacetylbaccatin III; 2-debenzoyl-2-(p-trifluoromethylbenzoyl)taxol; and 20-acetoxy-4-deacetyl-5-epi-20,O-secotaxol.

14. The method of claim 2 or 8 wherein the microtubule stabilizing anti-tumor agent is selected from the group consisting of arsenic trioxide, discodermolide, epothilone B, and (+)-14-normethyldiscodermolide.

15. The method of claim 2 or 8 wherein the microtubule stabilizing anti-tumor agent is taxol.

16. The method of claim 2 or 8 wherein the microtubule stabilizing anti-tumor agent is taxotere.

17. The method of claim 2 or 8 wherein the microtubule stabilizing anti-tumor agent is cephalomannine.

18. The method of claim 2 or 8 further comprising:
administering a nitric oxide synthetase (NOS) inhibitor to the mammal.

19. The method of claim 2 or 8 wherein the spores and microtubule stabilizing anti-tumor agent are administered serially.

20. The method of claim 18 wherein the spores, microtubule stabilizing anti-tumor agent and NOS inhibitor are administered serially.

21. The method of claim 2 or 8 wherein the toxicity of the toxin-defective *Clostridium novyi* is reduced by a factor of at least 2 compared to a corresponding *Clostridium novyi*.

* * * * *